US009566258B2

(12) United States Patent
Hou

(10) Patent No.: US 9,566,258 B2
(45) Date of Patent: *Feb. 14, 2017

(54) GASTRIC RETENTIVE PHARMACEUTICAL COMPOSITIONS FOR TREATMENT AND PREVENTION OF CNS DISORDERS

(71) Applicant: Depomed, Inc., Newark, CA (US)

(72) Inventor: Sui Yuen Eddie Hou, Foster City, CA (US)

(73) Assignee: Depomed, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,968

(22) Filed: Sep. 8, 2015

(65) Prior Publication Data

US 2015/0374653 A1 Dec. 31, 2015

Related U.S. Application Data

(63) Continuation of application No. 12/541,836, filed on Aug. 14, 2009, now Pat. No. 9,161,911.

(60) Provisional application No. 61/122,276, filed on Dec. 12, 2008, provisional application No. 61/089,339, filed on Aug. 15, 2008.

(51) Int. Cl.
| | | |
|---|---|---|
| *A61K 31/198* | (2006.01) | |
| *A61K 9/00* | (2006.01) | |
| *A61K 9/20* | (2006.01) | |
| *A61K 31/197* | (2006.01) | |
| *A61K 9/24* | (2006.01) | |

(52) U.S. Cl.
CPC .......... *A61K 31/197* (2013.01); *A61K 9/0065* (2013.01); *A61K 9/209* (2013.01); *A61K 9/2086* (2013.01); *A61K 31/198* (2013.01)

(58) Field of Classification Search
CPC .. A61K 9/0065; A61K 31/197; A61K 9/2086; A61K 9/209; A61K 31/198
See application file for complete search history.

(56) References Cited

U.S. PATENT DOCUMENTS

| | | | |
|---|---|---|---|
| 4,309,406 A | 1/1982 | Guley et al. | |
| 4,753,801 A | 6/1988 | Oren et al. | |
| 4,871,548 A | 10/1989 | Edgren et al. | |
| 4,900,755 A | 2/1990 | Dempski et al. | |
| 4,996,058 A | 2/1991 | Sinnreich | |
| 5,007,790 A | 4/1991 | Shell | |
| 5,192,550 A | 3/1993 | Edgren et al. | |
| 5,204,116 A | 4/1993 | Edgren et al. | |
| 5,443,843 A | 8/1995 | Curatolo et al. | |
| 5,445,829 A | 8/1995 | Paradissis et al. | |
| 5,582,837 A | 12/1996 | Shell | |
| 5,738,874 A | 4/1998 | Conte et al. | |
| 5,780,057 A | 7/1998 | Conte et al. | |
| 5,783,212 A | 7/1998 | Fassihi et al. | |
| 5,885,616 A | 3/1999 | Hsiao et al. | |
| 5,972,389 A | 10/1999 | Shell et al. | |
| 6,120,803 A | 9/2000 | Wong et al. | |
| 6,217,905 B1 | 4/2001 | Edgren et al. | |
| 6,238,699 B1 | 5/2001 | Rubin | |
| 6,294,200 B1 | 9/2001 | Conte et al. | |
| 6,372,254 B1 | 4/2002 | Ting et al. | |
| 6,372,255 B1 | 4/2002 | Saslawski et al. | |
| 6,488,962 B1 | 12/2002 | Berner et al. | |
| 6,531,158 B1 | 3/2003 | Teng et al. | |
| 6,548,083 B1 | 4/2003 | Wong et al. | |
| 6,602,521 B1 | 8/2003 | Ting et al. | |
| 6,635,280 B2 | 10/2003 | Shell et al. | |
| 6,635,281 B2 | 10/2003 | Wong et al. | |
| 6,682,759 B2 | 1/2004 | Lim et al. | |
| 6,723,340 B2 | 4/2004 | Gusler et al. | |
| 6,730,321 B2 | 5/2004 | Ting et al. | |
| 6,756,056 B2 | 6/2004 | Rubin | |
| 6,797,283 B1 | 9/2004 | Edgren et al. | |
| 6,881,420 B2 | 4/2005 | Flashner-Barak et al. | |
| 7,094,427 B2 | 8/2006 | Han et al. | |
| 7,438,927 B2 | 10/2008 | Berner et al. | |
| 7,514,100 B2 | 4/2009 | Oshlack et al. | |
| 7,612,112 B2 | 11/2009 | Berner et al. | |
| 2002/0119192 A1 | 8/2002 | Vishwanathan et al. | |
| 2002/0192290 A1 | 12/2002 | Seth | |
| 2003/0031711 A1 | 2/2003 | Fara et al. | |
| 2003/0044466 A1 | 3/2003 | Markey et al. | |
| 2003/0091630 A1 | 5/2003 | Berner et al. | |

(Continued)

FOREIGN PATENT DOCUMENTS

| | | |
|---|---|---|
| CA | 2143500 | 4/2007 |
| EP | 1568361 | 8/2005 |

(Continued)

OTHER PUBLICATIONS

Technical Data, DOW, POLYOX Water-Soluble Resins, Water Soluble-Resin Storage Stability, (2004).*
Stocchi et al., Arch Neurol., 62(6): 905-910 (2005).*
Kuoppamaki et al., Eur. J. Clin. Pharmacol., 65: 443-455 (2009).*
Clark, "Restless legs syndrome", J. Am. Board Fam. Med., vol. 14, No. 5, pp. 1-7 (2001).
Definition of "Restrictive", Collins English Dictionary, Harper Collins Publishers (2000).
DOW Chemical U.S.A. Product Information Publication dates Oct. 5, 2007, 34 pages (2007).
Grahnen et al., "Comparative multiple-dose bnarmacokinetics of controlled-release levodopa products", Eur. Neurol., vol. 32, No. 6, pp. 343-348 (1992).

(Continued)

*Primary Examiner* — Kortney L Klinkel
*Assistant Examiner* — Lisbeth C Robinson
(74) *Attorney, Agent, or Firm* — McDermott Will & Emery LLP

(57) ABSTRACT

The present disclosure is directed to methods and compositions for ameliorating, preventing and treating central nervous system (CNS) disorders. The invention aims to treat subjects suffering from, susceptible to, or diagnosed with CNS disorders, and in particular, to treating patients suffering from those disorders which are associated with neurotransmitter system dysfunction.

15 Claims, 11 Drawing Sheets

(56) References Cited

U.S. PATENT DOCUMENTS

| | | |
|---|---|---|
| 2003/0100611 A1 | 5/2003 | Berner et al. |
| 2003/0104053 A1 | 6/2003 | Gusler et al. |
| 2003/0104062 A1 | 6/2003 | Berner et al. |
| 2003/0133985 A1 | 7/2003 | Berner et al. |
| 2003/0147957 A1 | 8/2003 | Licht et al. |
| 2003/0152628 A1 | 8/2003 | Licht et al. |
| 2003/0224045 A1 | 12/2003 | Han et al. |
| 2004/0052843 A1 | 3/2004 | Lerner et al. |
| 2004/0062802 A1 | 4/2004 | Hermelin |
| 2004/0180086 A1 | 9/2004 | Ramtoola et al. |
| 2004/0180088 A1 | 9/2004 | Dudhara et al. |
| 2004/0185105 A1 | 9/2004 | Berner et al. |
| 2004/0234608 A1 | 11/2004 | Fleshner-Barak et al. |
| 2005/0064036 A1 | 3/2005 | Berner et al. |
| 2005/0100602 A1 | 5/2005 | Sako et al. |
| 2005/0163850 A1 | 7/2005 | Wong et al. |
| 2006/0013875 A1 | 1/2006 | Han et al. |
| 2006/0045865 A1 | 3/2006 | Jacob et al. |
| 2006/0099245 A1 | 5/2006 | Kumar et al. |
| 2008/0107732 A1 | 5/2008 | Dharmadhikari et al. |
| 2008/0139655 A1 | 6/2008 | Bortz et al. |
| 2009/0028941 A1 | 1/2009 | Cowles et al. |

FOREIGN PATENT DOCUMENTS

| | | |
|---|---|---|
| EP | 2105133 | 9/2009 |
| JP | 2005-528430 A | 9/2005 |
| JP | 2005-532985 A | 11/2005 |
| JP | 2011-518148 A | 6/2011 |
| WO | WO 99/17745 | 4/1999 |
| WO | WO 00/15197 | 3/2000 |
| WO | WO 01/10419 A1 | 2/2001 |
| WO | WO 02/00213 | 1/2002 |
| WO | WO 03/005967 A2 | 1/2003 |
| WO | WO 03/035041 A1 | 5/2003 |
| WO | WO 03/035177 A2 | 5/2003 |
| WO | WO 03/075893 A1 | 9/2003 |
| WO | WO 03/101432 A1 | 12/2003 |
| WO | WO 2004/032906 A1 | 4/2004 |
| WO | WO 2008/030830 A2 | 3/2008 |
| WO | WO 2008/079404 A1 | 7/2008 |
| WO | WO 2008/087882 A1 | 7/2008 |
| WO | WO 2009/144558 A1 | 12/2009 |

OTHER PUBLICATIONS

International Search Report and Written Opinion from PCT Patent Application No. PCT/US2009/053937 mailed Nov. 2, 2009.

Klausner et al., "Novel levodopa oastroretentive dosage form: in-vivo evaluation in dogs", J. Control. Rel., vol. 88, No. 1, pp. 117-126 (2003).

Nyholm, "Pharmaookinetic optimisation in the treatment of parkinson's disease: an update", Clin. Pharm. vol. 45, No. 2, pp. 109-136 (2006).

\* cited by examiner

GASTRIC RETENTIVE PHARMACEUTICAL COMPOSITIONS FOR TREATMENT AND PREVENTION OF CNS DISORDERS

CROSS-REFERENCE TO RELATED APPLICATIONS

This application is a continuation of U.S. application Ser. No. 12/541,836, filed Aug. 14, 2009 which claims priority to U.S. Provisional Application No. 61/122,276, filed on Dec. 12, 2008, and U.S. Provisional Application No. 61/089,339, filed Aug. 15, 2008, the disclosures of which are all incorporated herein by reference in their entirety.

TECHNICAL FIELD

The present disclosure is directed to gastric retained pharmaceutical compositions and related methods useful in ameliorating, preventing and treating central nervous system (CNS) disorders. The described invention aims to treat patients suffering from, susceptible to, or diagnosed with CNS disorders, and in particular, to treating patients suffering from those disorders which are associated with neurotransmitter system dysfunction, which include, for example, neurodegenerative diseases including presenile dementia, senile dementia of the Alzheimer's type, and Parkinsonism including Parkinson's disease, and other CNS disorders including attention deficit disorder, schizophrenia and Tourette's syndrome.

BACKGROUND

CNS disorders are a type of neurological disorder. CNS disorders can be drug induced, can be attributed to genetic predisposition, infection or trauma, or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Parkinson's disease (PD) is a debilitating neurodegenerative disease, presently of unknown etiology, characterized by tremors and muscular rigidity. A feature of the disease appears to involve the degenerative of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., Brain Res., Vol. 54, pp. 167-170 (1991) and Clark, et al., Br. J. Pharm., Vol. 85, pp. 827-835 (1985). It also has been proposed that nicotine can ameliorate the symptoms of PD. See, Smith et al., Rev. Neurosci., Vol. 3(1), pp. 25-43 (1982).

The combination of levodopa and carbidopa in considered to be the most effective treatment for symptoms of Parkinson's disease (The Medical Letter, 35:31-34), 1993). For subjects afflicted with and/or diagnosed with Parkinson's disease, the benchmark treatment is typically oral administration of a dosage form containing levodopa in combination with carbidopa. Levodopa is a precursor of dopamine but unlike dopamine, is able to cross the blood brain barrier. However, while in the peripheral blood system and prior to crossing the blood brain barrier, levodopa is decarboxylated into dopamine. Carbidopa inhibits the rapid peripheral decarboxylation of levodopa into dopamine. The negates the need for high doses of levodopa which would result in adverse events, i.e., side effects, in particular nausea, caused by the dopamine released into the circulation from levodopa conversion in the intestinal mucosa and other peripheral tissues. Currently, oral levodopa/carbidopa combination drug products on the market consist of immediate release tables, for example, Sinemet® and Atamet®, and extended release tables, for example, Sinemet® CR and generics. Carbidopa is also available as single-ingredient tablets for those patients who require additional carbidopa when taking the combination tablets.

Immediate release levodopa/carbidopa tablets are administered three or four times a day and the extended release product is administered two to three times a day. Recently, an external pump that infuses levodopa and carbidopa into the duodenum at a controlled rate through a surgical opening in the stomach became available in Europe and Canada (Duodopa®, Solvay Pharmaceuticals, Germany).

It is know that exposure of affected neurons in Parkinson's disease to exogenous dopamine in a pulsatile fashion, such as in oral administration of levodopa in immediate release form to Parkinson's patients, eventually, in two to three years, leads to the development of the "on-off" phenomenon, i.e., mobility is improved for a couple of hours after each dose, but rigidity and akinesia return at the end of the dosing interval. Dosing more frequently would improve this but dyskinesia, excessive and abnormal involuntary movement, would occur when levodopa level becomes high. It is also know that when levodopa levels are maintained constant by IV infusion at a constant rate, the on-off phenomena and dyskinesia are reduced. This is also mimicked by taking subdivided daily oral doses frequently, such as every two hours instead of four or six hours. The later can in theory be realized in an oral extended release dosage forms. However, the unique oral absorption characteristics of levodopa have present problems in achieving an oral extended/controlled release dosage form that delivers the drug at a relatively constant rate for an extended period of time to achieve relatively constant plasma levels of levodopa.

As levodopa is only absorbed in the proximal small intestine via an active transport mechanism for aromatic amino acids, this limits the performance of conventional oral controlled release dosage forms which are rapidly emptied from the stomach into the intestine. If the duration of release is long compared to the transit time through the small intestine, about 2 to 3 hours, most of the drug is not delivered to the site of absorption in the proximal small intestine and is not absorbed. Hence, the duration of release in the small intestine has to be relatively short in order not to lose bioavailability.

Such is the case for SINEMET® CR, for which complete in vitro release (dissolution apparatus 1, paddle, pH 1) occurs in about 2.5 hours. Formulations with longer release durations resulted in lower bioavailability of levodopa. Even so, SINEMET® CR bioavailability is only 70-75% of the immediate release tablet SINEMET®. Administration with food increases the bioavailability substantially since gastric emptying is slowed. Despite FDA recommended dosing of the drug two to three times a day, in actual clinical practice, some patients may require administration of the drug four to six times a day due.

A duodenum infusion pump can deliver levodopa and carbidopa, at a constant rate, directly to the intestinal site of absorption thereby mitigating the above problems. But such therapy is neither convenient in initiation (surgical insertion of infusion tubing) nor in maintenance (wound and device care).

Thus, there is a strong need in the art for pharmaceutical compositions that effectively and conveniently aide in the treatment and prevention of movement disorders, such as Parkinson's Disease, by providing extended/controlled release of levodopa and carbidopa at a relatively constant rate for an extended period of time to achieve relatively constant plasma levels. The present disclosure meets these needs, among others.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF SUMMARY

The following aspects and embodiments thereof described and illustrated below are meant to be exemplary and illustrative, not limiting in scope.

In one aspect a gastric-retentive ("GR") dosage form comprising a therapeutically effective amount of levodopa and carbidopa for oral administration to a subject, such as a human patient, suffering from a movement disorder.

In one embodiment, the dosage form comprises a first dose of levodopa and a first dose of carbidopa. In another embodiment, the first dose of levodopa and the first dose of carbidopa are dispersed in a polymer matrix. In another embodiment, the polymer matrix comprises at least one hydrophilic polymer. In yet another embodiment, the polymer matrix swells upon imbibition of fluid to a size sufficient for gastric retention in the stomach of a subject in a fed mode.

In one embodiment, the GR dosage form is a single layer or monolithic dosage form comprising a first dose of levodopa and a first dose of carbidopa as an extended release ("ER") dosage form. In another embodiment, the GR dosage form has a total weight of about 400 mg to about 900 mg, or about 500 mg to about 800 mg. In another embodiment, the GR dosage form has a total weight of about 400 mg, 550 mg, 600 mg, 650 mg, 700 mg, 750 mg, 800 mg, 850 mg, or 900 mg.

In one embodiment, the first dose of levodopa is about 100 mg to about 500 mg or about 200 mg to about 300 mg. In another embodiment, the first dose of levodopa is about 250 mg to about 350 mg or about 200 mg to about 300 mg.

In yet another embodiment, the first dose of levodopa is about 125 mg, 150 mg, 175 mg, 200 mg 220 mg, 240 mg, 250 mg, 260 mg, 275 mg, 300 mg, 325 mg, 350 mg, 375 mg, 400 mg, 425 mg, 450 mg, 475 mg, or 500 mg.

In one embodiment, the first dose of carbidopa is about 25 mg to about 125 mg or about 50 mg to about 75 mg. In another embodiment, the first dose of levodopa is about 60 mg to about 90 mg or about 50 mg to about 75 mg. In yet another embodiment, the first dose of levodopa is about 30 mg, 40 mg, 45 mg, 50 mg, 55 mg, 60 mg, 65 mg, 70 mg, 75 mg, 80 mg, 85 mg, 90 mg, 95 mg, 100 mg, 110 mg, or 130 mg.

In one embodiment, the ratio of the first dose of levodopa to the first dose of carbidopa ranges from about 10:1 to about 1:10. In another embodiment, the ratio is 10:1, 9:1, 8:1, 7:1, 6:1, 5:1, 4:1, 3:1 or 2:1.

In one embodiment, the dosage form further comprises an antioxidant. In another embodiment, the antioxidant is selected from the group consisting of tocopherol, sodium metabisulphite, butylated hydroxytoluene (BHT), citric acid, cysteine HCl, butylated hydroxyanisole, ascorbic acid and sodium ascorbate, propyl gallat, sodium sulfite, tocopherol, and sodium metabisulphite. In yet another embodiment, the antioxidant is present in the dosage for at a wt % (weight percent) of approximately 0.01 wt %, 0.05 wt %, 0.1 wt %, 0.5 wt %, 0.75 wt %, 1 wt %, 2 wt %, 3 wt % or 4 wt %.

In one embodiment, the at least one hydrophilic polymer comprises a mixture of one or more different hydrophilic polymers. In another embodiment, the at least one hydrophilic polymer is selected from the group consisting of polyethylene oxide) (PEO), wherein the PEO has a molecular weight ranging from about 300,000 daltons to about 2,000,000 Da (Daltons). In another embodiment, the PEO has a molecular weight ranging from about 900,000 daltons to about 4,000,000 daltons. In yet another embodiment, the molecular weight of the PEO has a molecular weight of approximately 600,000 Da, 900,000 Da, 1,000,000 Da, 2,000,000 Da, 4,000,000 Da, 5,000,000 Da, 7,000,000 Da, 9,000,000 Da, 10,000,000 Da or 12,000,000 Da.

In one embodiment, the at least one hydrophilic polymer is present in the dosage form in an amount ranging from about 15 wt % to about 70 wt %. In another embodiment, the at least one hydrophilic polymer is present in the dosage form in an amount ranging from about 15 wt % to about 65 wt %. In yet another embodiment, the at least one hydrophilic polymer is present in the dosage form in an amount ranging from about 20 wt % to about 60 wt %. In still another embodiment, the at least one hydrophilic polymer is present in the dosage form in an amount ranging from about 30 wt % to about 50 wt %. In still another embodiment, the at least one hydrophilic polymer is present in the dosage form in about 20 wt %, 25 wt %, 30 wt %, 35 wt %, 40 wt %, 45 wt %, 50 wt %, 55 wt %, or 60 wt %.

In one embodiment, the GR dosage form further comprises a binder. In another embodiment, the binder is povidone (PVP) or hydroxypropylcellulose (HPC). In yet another embodiment, the GR dosage form comprises a binder that is present in an amount ranging from about 0.1 wt % to about 20 wt % or in an amount ranging from about 2 wt % to about 15 wt %, or in an amount ranging from about 2 wt % to about 8 wt %. In still another embodiment, the GR dosage form comprises a binder that is present in an amount that is about 1.0 wt %, 1.1 wt %, 1.2 w %, 1.4 wt %, 1.5 wt %, 1.7 wt %, 1.8 wt %, 1.9 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt % or 8.0 wt % of the ER portion.

In one embodiment, the GR dosage form further comprises a filler. In another embodiment, the filler is microcrystalline cellulose (MCC) and/or mannitol. In another embodiment, the GR dosage form comprises about 35 wt % to about 85 wt %, about 45 wt % to about 75 wt %, about 50 wt % to about 65 wt % filler. In another embodiment, the GR dosage form comprises a filler that is present in an amount that is about 45 wt %, 50 wt %, 51 wt %, 52 wt %, 53 wt %, 55 wt %, 60 wt %, 65 wt %, 68 wt %, 68 wt %, 70 wt %, 71 wt %, 72 wt %, 75 wt %, 80 wt %, or 85 wt % of the dosage form.

In one embodiment, the ER portion of the dosage form further comprises a lubricant. In another embodiment, the lubricant is magnesium stearate. In another embodiment, the ER portion of the dosage form comprises a lubricant that is present in an amount ranging from about 0.5% to about 5.0%. In yet another embodiment, the ER portion of the dosage form comprises a lubricant that is present in an amount that is about 0.1 wt %, 0.5 wt %, 0.75 wt %, 1.0 wt %, 1.5 wt %, 1.75 wt %, 1.80 wt %, 1.85 wt %, 1.90 wt % or 2.0 wt % of the ER portion.

In one embodiment, the ER portion of the dosage form comprises a color agent. In another embodiment, the color agent is present in an amount that is about 2.0-5.0 wt % of the ER portion of the dosage form. In yet another embodiment, the color agent is present in an amount that is about 1.0, 1.5, 2.0, 2.5, 3.0, 3.5, 4.0, 4.5, or 5.0 wt % of the ER portion.

In one embodiment, the dosage form imbibes fluid and swells to a size between about 110% to about 170% of the size of the dosage form prior to imbibition of fluid. In another embodiment, the dosage form swells to a size between about 115% to about 150% of the size of the dosage form prior to imbibition of fluid. In yet another embodiment, the dosage form imbibes fluid and swells to a size between about 110% to about 170%, between about 115% to about 165%, between about 120% to about 150%, between about 125% to about 140% of the size of the dosage form prior to imbibition of fluid within 30 minutes of administration or within about 30 minutes of the start of imbibition of fluid into the dosage form.

In one embodiment, the dosage form begins to erode upon swelling of the dosage form. In another embodiment, the dosage form erodes such that the size of the dosage form begins to decrease after the first 30 minutes after administration or after the first 30 minutes after the start of imbibition of fluid into the dosage form.

In another embodiment, upon administering of the dosage form to a subject, the dosage form provides at least about 3 to about 8 hours of drug delivery to the upper gastrointestinal tract, which includes the stomach and the small intestine. In another embodiment, the dosage form provides at least 4 hours, at least 6 hours or at least 8 hours of drug delivery to the upper gastrointestinal tract. In yet a further embodiment, the dosage form provides at least about 6 hours to about 8 hours of drug delivery to the upper gastrointestinal tract. In yet a further embodiment, the dosage form provides at least about 3, 4, 5, 6, 7, or 8 hours of drug delivery to the upper gastrointestinal tract.

In one embodiment, the dosage form releases substantially all of the first dose of levodopa and substantially all of the first dose of carbidopa over a period of between about 6 and 12 hours, between about 8 and 10 hours, or between about 7 and 9 hours. In another embodiment, the dosage form releases substantially all of the first dose of levodopa and substantially all of the first dose of carbidopa over a period of about 6 hours, 7 hours, 8 hours, 9 hours, 10 hours, 11 hours, 12 hours, or 13 hours. In yet another embodiment, the dosage form releases at least about 65%, 70%, 75%, 80%, 85%, 90%, 95%, or 98% of the first dose of levodopa and the first dose of carbidopa during a time period of about 6 hours, 7 hours, 8 hours, 9 hours, 10 hours, 11 hours, 12 hours, or 13 hours after oral administration of the dosage form.

In one embodiment, in an in vitro dissolution test, the dosage form releases about 15% to about 50% of the first dose of levodopa and about 15% to about 50% of the first dose of carbidopa within about 1 hour of the start of the dissolution test. In another embodiment, in an in vitro dissolution test, the dosage form releases about 20% to about 40% of the first dose levodopa and about 20% to about 40% of the first dose of carbidopa within about 1 hour of the start of the dissolution test. In one embodiment, between about 10% to about 40% of the levodopa is released within about 1 hour in an in vitro dissolution test.

In some embodiments, the dosage form provides an in vitro dissolution profile wherein for each of the first dose of levodopa and the first dose of the carbidopa, between about 40% to about 50% of the first dose remains in the dosage form between about 1 and 2 hours after administration. In one embodiment, not more than 30% of the first dose of levodopa and first dose of carbidopa is released within about the first hour. In a further embodiment, not more than 40% of the first dose of levodopa and first dose of carbidopa is released within about the first hour. In another embodiment, not more than 85% of the first dose of levodopa and first dose of carbidopa is released within about 4 hours. In another embodiment, not less than 50% is released after about 4 hours. In yet another embodiment, not less than 60% is released after about 6 hours.

In one embodiment the in vitro dissolution test is a USP Type I dissolution test performed at 37° C. in an aqueous medium containing 0.1N HCl. In another embodiment, the USP Type I dissolution test is run at a speed of 150 rpm.

In one embodiment the in vitro dissolution test is a USP Type 11 dissolution test performed at 37° C. in an aqueous medium containing 0.1N HCl. In another embodiment, the USP Type II dissolution test is run at a speed of 150 rpm.

In one another embodiment the in vitro dissolution test is a USP Type III dissolution test performed at 37° C. in an aqueous medium containing 0.1N HCl. In another embodiment, the USP Type III dissolution test is run at a speed of 10 dpm.

In one embodiment, the dosage form, when orally administered to a subject in a fed mode, produces a plasma profile in the subject wherein the plasma level of levodopa is maintained for at least about 6 to about 10 hours, about 8 to about 12 hours, about 6 to about 8 hours, or about 7 to about 9 hours.

In one embodiment, the dosage form, when orally administered to a subject in a fed mode, results in an AUC for a 12-hour dosing interval is between about 300 ng·hour/ml to about 1500 ng·hour/ml. In another embodiment, the AUC for a 12-hour dosing interval is between about 400 ng·hour/ml to about 800 ng·hour/ml. In yet another embodiment, the AUC for a 12-hour dosing interval is between about 500 ng·hour/ml to about 700 ng·hour/ml.

In one embodiment, the dosage form when administered to the subject produces a plasma profile in the subject comprising a prolonged plasma level of levodopa for at least 6-10 hours or 8-12 hours maintaining therapeutic efficacy;

and a $C_{max}$ for levodopa of between about 300 ng/ml to about 1500 ng/ml and a $C_{min}$ for levodopa of between about 300 ng/ml to about 3000 ng/ml. In another embodiment, the ratio of the $C_{max}$ to the $C_{min}$ is less than or equal to about 4.

In one embodiment, the dosage form when administered to the subject produces a plasma profile in a human patient comprising a fast onset plasma level achieved within less than about two hours followed by a prolonged plasma level of levodopa for at least 6-10 hours or 8-12 hours maintaining therapeutic efficacy; and a $C_{max}$ for levodopa of between about 300 ng/ml to about 1500 ng/ml of levodopa for at least 6-10 hours or 8-12 hours maintaining therapeutic efficacy. In another embodiment, the ratio of the $C_{max}$ to the $C_{min}$ is less than or equal to about 5.

In one embodiment, the ratio of the $C_{max}$ to the $C_{min}$ during a 12-hour dosing interval is between about 3 to 5. In another embodiment, the ratio is greater than 1 but less than about 20, or is greater than 1 but less than or equal to about 4. In yet another embodiment, the ratio is between about 1 to about 4.

In another aspect, the dosage form further comprises a second dose of levodopa and a second dose of carbidopa which are present in an immediate release ("IR") portion.

In one embodiment, the GR dosage form comprises an ER portion comprising a first dose of levodopa and a first dose of carbidopa, and an IR portion comprising a second dose of levodopa and a second dose of carbidopa. In another embodiment, the GR dosage form is a bilayer tablet, wherein the first layer is the ER portion and the second layer is the IR portion. In yet another embodiment, the GR dosage form is a capsule which comprises an ER portion and an IR portion.

In one embodiment, the ratio of the second dose of levodopa to the second dose of carbidopa ranges from about 10:1 to about 1:10. In another embodiment, the ratio is about 10:1, 9:1, 8:1, 7:1, 6:1, 5:1, 4:1, 3:1 or 2:1.

In one embodiment, the ratio of the first dose of levodopa to the first dose of carbidopa in the ER portion is lower than the ratio of the second dosage of levodopa to the second dose of carbidopa in the IR portion. In another embodiment the ratio of the first dose of levodopa to the first dose of carbidopa in the ER portion is about 3:1 and the ratio of the second dosage of levodopa to the second dose of carbidopa in the IR portion is 4:1. In yet another embodiment the ratio of the first dose of levodopa to the first dose of carbidopa in the ER portion is about 3:1 and the ratio of the second dosage of levodopa to the second dose of carbidopa in the IR portion is about 5:1.

In one embodiment, the ratio of the first dose of levodopa to the first dose of carbidopa in the ER portion is greater than the ratio of the second dosage of levodopa to the second dose of carbidopa in the IR portion. In another embodiment, the ratio of the first dose of levodopa to the first dose of carbidopa in the ER portion is about 4:1 and the ratio of the second dosage of levodopa to the second dose of carbidopa in the IR portion is about 3:1. In yet another embodiment the ratio of the first dose of levodopa to the first dose of carbidopa in the ER portion is 4:1 and the ratio of the second dosage of levodopa to the second dose of carbidopa in the IR portion is 2:1.

In one embodiment, the second dose of levodopa is about 50 mg to about 150 mg or about 20 mg to about 100 mg. In another embodiment, the second dose of levodopa is about 75 mg to about 125 mg or about 40 mg to about 70 mg. In yet another embodiment, the second dose of levodopa is about 40 mg, 45 mg, 50 mg, 55 mg 60 mg, 65 mg, 70 mg, 75 mg, 80 mg, 85 mg, 90 mg, 95 mg, 100 mg, 105 mg, 110 mg, 115 mg, 120 mg, or 125 mg.

In one embodiment, the second dose of carbidopa is about 15 mg to about 50 mg or about 5 mg to about 25 mg. In another embodiment, the second dose of levodopa is about 25 mg to about 40 mg or about 15 mg to about 25 mg. In yet another embodiment, the second dose of levodopa is about 30 mg, 40 mg, 45 mg, 50 mg, 55 mg, 60 mg, 65 mg, 70 mg, 75 mg, 80 mg, 85 mg, 90 mg, 95 mg, 100 mg, 110 mg, or 130 mg.

In one embodiment, the ER portion comprises about 300 mg levodopa and about 75 mg carbidopa and the IR portion comprises about 100 mg levodopa and about 35 mg carbidopa. In another embodiment, the ER portion comprises about 240 mg levodopa and about 60 mg carbidopa and the IR portion comprises about 60 mg levodopa and the IR portion comprises about 20 mg carbidopa.

In one embodiment, substantially all of the second dose of levodopa and the second dose of carbidopa are released from the IR portion in about 1 to about 5 minutes, or in about 2 to about 4 minutes after oral administration. In another embodiment, substantially all of the second dose of levodopa and the second dose of carbidopa are released from the IR portion within about 2 minutes, 3 minutes, 4 minutes, 5 minutes, 6 minutes, 7 minutes, or 8 minutes after oral administration.

In yet another embodiment, the IR portion of the dosage form further comprises a binder. In some embodiments, the binder is chosen from among povidone and hydroxypropylcellulose. In another embodiment, the binder is present in the IR portion of the dosage form in an amount that is about 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt % or 10.0 wt % of the IR portion.

In one embodiment, the IR portion of the dosage form further comprises a filler. In another embodiment, the filler is microcrystalline cellulose (MCC) and/or mannitol. In another embodiment, the IR portion of the dosage form comprises about 35 wt % to about 85 wt %, about 45 wt % to about 75 wt %, about 50 wt % to about 65 wt % filler. In another embodiment, the IR portion of the dosage form comprises a filler that is present in an amount that is about 45 wt %, 50 wt %, 51 wt %, 52 wt %, 53 wt %, 55 wt %, 60 wt %, 65 wt %, 68 wt %, 68 wt %, 70 wt %, 71 wt %, 72 wt %, 75 wt %, 80 wt %, or 85 wt % of the dosage form.

In one embodiment, the IR portion of the dosage form comprises a color agent. In another embodiment, the color agent is present in an amount that is about 2.0-5.0 wt % of the IR portion of the dosage form. In yet another embodiment, the color agent is present in an amount that is about 1.0, 1.5, 2.0, 2.5, 3.0, 3.5, 4.0, 4.5, or 5.0 wt % of the IR portion.

In some embodiments, the bilayer tablet has a friability of no greater than about 0.1%, 0.2% 0.3%, 0.4%, 0.5%, 0.7% or 1.0%.

In some embodiments, the bilayer tablet has a hardness of at least about 10 kilopond (also known as kilopons) (kp). In some embodiments, the tablet has a hardness of about 9 kp to about 25 kp, or about 12 kp to about 20 kp. In further embodiments, the tablet has a hardness of about 11, 12, 13, 14, 15, or 16 kp.

In some embodiments, the tablets have a content uniformity of from about 85 to about 115 percent by weight or from about 90 to about 110 percent by weight, or from about 95 to about 105 percent by weight. In other embodiments, the content uniformity has a relative standard deviation (RSD) equal to or less than about 3.5%, 3.0%, 2.5%, 2.0%, 1.5%, 1.0% or 0.5%.

In one embodiment, the IR portion further comprises an antioxidant chosen from tocopherol, sodium metabisulphite, butylated hydroxytoluene (BHT), citric acid, cysteine HCl, butylated hydroxyanisole, ascorbic acid and sodium ascorbate, and sodium metabisulphite. In yet another embodiment, the antioxidant is present in the dosage for at a wt % (weight percent) of approximately 0.01 wt %, 0.05 wt %, 0.1 wt %, 0.5 wt %, 0.75 wt %, 1 wt %, 2 wt %, 3 wt % or 4 wt %.

In another aspect, a pharmaceutical or gastric retentive oral dosage form comprising levodopa and carbidopa, wherein the formulation is administered to a mammal two times in a 24 hour period (b.i.d. or twice-daily) or three times in a 24 hour period (t.i.d. or three times daily) is provided.

In one embodiment, the dosage form comprising an ER portion and an IR portion produces a plasma profile in the subject comprising a fast onset plasma level, wherein a therapeutically effective amount of levodopa is present in the blood plasma within less than about 0.5 hours, 1 hour, 1.5 hours or 2 hours after oral administration of the dosage form, followed by a prolonged plasma level of levodopa for a period of at least about 6 to about 10 hours or about 8 to about 12 hours. In one embodiment, the prolonged plasma level of levodopa is maintained at a level which is no less than 95%, 90%, 85%, 80%, 75% or 70% of the $C_{max}$ achieved within about 12 hours of administration of the oral dosage form. In another embodiment, the prolonged plasma level of levodopa is maintained for a period of about 6 hours, 7 hours, 8 hours, 9 hours, 10 hours, 11 hours, 12 hours or 13 hours after oral administration of the dosage form.

Also provided is a method of treating a subject suffering from a movement disorder, comprising administering a therapeutic effective amount of any of the describe dosage forms or pharmaceutical formulations herein.

In one embodiment, the subject is suffering from a movement disorder including but not limited to Parkinson's Disease, Restless Leg Syndrome (RLS), Huntington's chorea, progressive supranuclear palsy, Wilson's disease, Tourette's syndrome, epilepsy, tardive dyskinesia, residual amblyopia, Angelman Syndrome, and various chronic tremors, tics and dystonias.

In one embodiment is a method for treating Parkinson's Disease (PD) by administering a dosage form providing both immediate release and sustained release of levodopa and carbidopa.

In one embodiment, a gastric retained dosage form comprising levodopa, carbidopa, and a swellable polymer is administered to a subject suffering from or diagnosed with a movement disorder. In another embodiment, the gastric retained dosage form comprises an ER portion as described above. In yet another embodiment, the gastric retained dosage form further comprises an IR portion as described above.

In one embodiment, the gastric retained dosage form comprises about 300 mg levodopa and about 80 mg carbidopa. In another embodiment, the gastric retained dosage form comprises about 400 mg levodopa and about 110 mg carbidopa.

In one embodiment, a gastric retained dosage form is administered to a subject in a fed mode. In another embodiment, the dosage form is administered with a meal to the subject twice in a 24 hour period. In some embodiments, the dosage form is administered with a meal to the subject three times in a 24 hour period.

Also provided, is a method of making a pharmaceutical or gastric retentive dosage form comprising a first dose of levodopa, a first dose of carbidopa dispersed in an ER polymer matrix comprised of a polymer that swells upon imbibition of fluid to a size sufficient for gastric retention in the upper gastrointestinal tract in a fed mode.

In some embodiments, the method comprises wet granulating a first mixture that comprises levodopa, carbidopa and a binder to produce a first granulation mixture. In another embodiment, the wet granulating comprises spraying a solution of binder dissolved in water onto levodopa particles. In a further embodiment, the particles of the first granulation mixture are blended with a polymer and one or more excipients to form an ER portion of a dosage form.

In some embodiments, the one or more excipients blended with the first granulation mixture are chosen from among a filler, a lubricant and a color agent.

In further embodiments, the wet granulating is a fluid bed granulation method. In other embodiments, the wet granulating is a high shear granulation method.

In a further embodiment, the method comprises compressing the ER portion of the dosage form into a tablet.

In some embodiments, the wet granulation of the ER portion of the dosage form produces particles with a bulk density ranging from about 0.30 to 0.40 grams/milliliter (g/ml). In other aspects, the wet granulation produces particles with a tap density ranging from about 0.35 g/ml to about 0.45 g/ml. In other embodiments, the wet granulation produces particles, wherein at least about 50% of the particles have a size greater than 250μ. In still other embodiments, the wet granulation produces particles wherein about 20% to about 30% of the particles have a size greater than about 150μ and less than about 250μ.

In one embodiment, the method of making a pharmaceutical and/or gastric retentive oral dosage form comprising levodopa and carbidopa further comprises wet granulating a second mixture comprising the levodopa, the carbidopa, and the binder to form a second granulation mixture. In a further embodiment, the second granulation mixture is blended with one or more excipients to produce an IR portion of the dosage form. In yet a further embodiment, the IR portion is compressed with the ER portion of the dosage form to produce a bilayer tablet.

In further embodiments, wet granulating the second mixture is achieved by fluid bed granulation. In other embodiments, wet granulating the second mixture is achieved by a high shear granulation method.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

In any one of the above methods, one embodiment is a gastric retentive dosage form comprised of a dose of gabapentin and a hydrophilic swellable polymer, wherein the dosage form after administration swells to a size that is retained in the stomach in fed mode.

In addition to the exemplary aspects and embodiments described above, further embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention.

DETAILED DESCRIPTION

Figure 1:
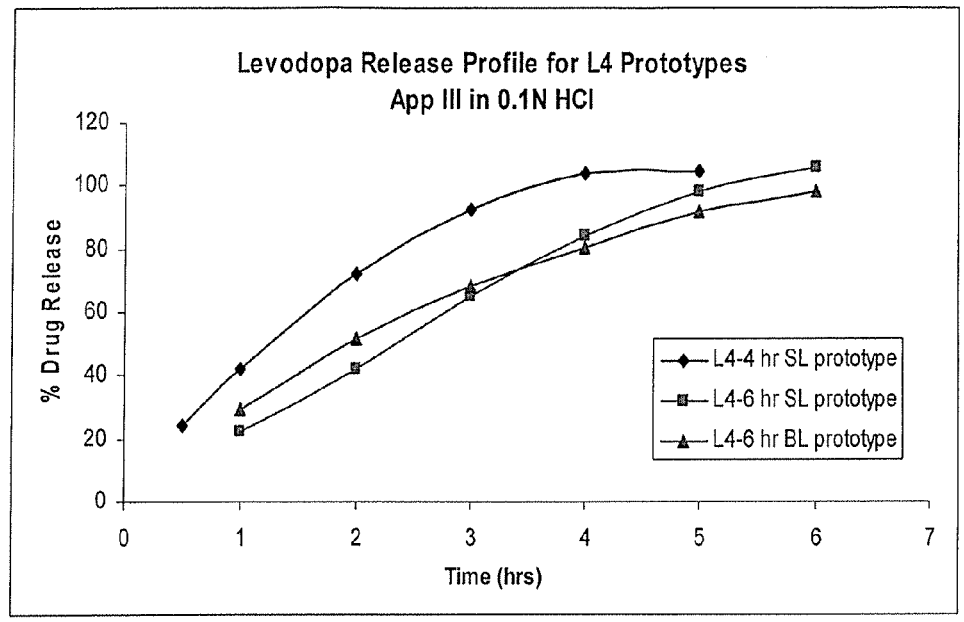
FIG. 1 shows the in vitro release profile for levodopa release from the LC4SL dosage form as determined using a USP Dissolution Apparatus III at 37.0±0.5° C.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety.

DEFINITIONS

In describing and claiming the present subject matter, the following terminology will be used in accordance with the definitions described below.

As used in this specification and the appended claims, the singular forms "a," "an" and "the" include plural referents unless the context clearly dictates otherwise; thus, for example, reference to "an active agent" or "a pharmacologically active agent" includes a single active agent as well a two or more different active agents in combination, reference to "a polymer" includes mixtures of two or more polymers as well as a single polymer, and the like.

As used herein, the phrases "for example," "for instance," "such as," and "including" are meant to introduce examples to illustrate more general subject matter. These examples are provided only as an aid for understanding the disclosure, and are not meant to be limiting in any fashion.

The term "about," particularly in reference to a given quantity, is meant to encompass deviations of plus or minus five percent.

Compounds useful in the dosage forms described herein include those noted herein in any of their pharmaceutically acceptable forms, including isomers such as diastereomers and enantiomers, salts, solvates, and polymorphs, as well as racemic mixtures and pure isomers of the compounds described herein, where applicable.

The term "controlled release" is intended to refer to any dosage form in which release of the drug is not immediate, i.e., with a "controlled release" formulation, oral administration does not result in immediate release of the drug into an absorption pool. The term is used interchangeably with "nonimmediate release" as defined in Remington: The Science and Practice of Pharmacy, $20^{th}$ edition (Lippincott Williams & Wilkins, 2000). Examples of controlled release dosage forms include "delayed release," "sustained release," "extended release," and "modified release" dosage forms. In general, however, the term "controlled release" as used herein includes any nonimmediate release formulation.

The terms "effective amount" or a "therapeutically effective amount" refer to the amount of drug or pharmacologically active agent to provide the desired effect without toxic effects. The amount of an agent that is "effective" may vary from individual to individual, depending on the age, weight, general condition, and other factors of the individual, or depending on the type and severity of the disorder or disease being treated. An appropriate "effective" amount in any individual may be determined by one of ordinary skill in the art using routine experimentation. An "effective amount" of an agent can refer to an amount that is either therapeutically effective or prophylactically effective or both.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. The term "pharmacologically active" (or simply "active") as in a "pharmacologically active" derivative, refers to a derivative having the same type of pharmacological activity as the parent compound and/or drug and approximately equivalent in degree. When the term "pharmaceutically acceptable" is used to refer to a derivative (e.g., a salt) of an active agent, it is to be understood that the compound is pharmacologically active as well. When the term, "pharmaceutically acceptable" is used to refer to an excipient, it implies that the excipient has met the required standards of toxicological and manufacturing testing or that it is on the Inactive Ingredient Guide prepared by the FDA, or comparable agency.

The terms "drug," "active agent," "therapeutic agent," and/or "pharmacologically active agent" are used interchangeably herein to refer to any chemical compound, complex or composition that is suitable for oral administration and that has a beneficial biological effect, preferably a therapeutic effect in the treatment or prevention of a disease or abnormal physiological condition. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

The term "dosage form" refers to the physical formulation of the drug for administration to the patient. Dosage forms include without limitation, tablets, capsules, caplets, liquids, syrups, lotions, lozenges, aerosols, patches, enemas, oils, ointments, pastes, powders for reconstitution, sachets, solutions, sponges, and wipes. Within the context of the present invention, a dosage form comprising a levodopa/carbidopa formulation will generally be administered to patients in the form of tablets or capsules, although a liquid formulation is also contemplated under the invention.

The term "dosage unit" refers to a single unit of the dosage form that is to be administered to the patient. The dosage unit will be typically formulated to include an amount of drug sufficient to achieve a therapeutic effect with a single administration of the dosage unit although where the size of the dosage form is at issue, more than one dosage unit may be necessary to achieve the desired therapeutic effect. For example, a single dosage unit of a drug is typically, one tablet, one capsule, or one tablespoon of liquid. More than one dosage unit may be necessary to administer sufficient drug to achieve a therapeutic effect where the amount of drug causes physical constraints on the size of the dosage form.

"Total daily dose" is the total amount of drug administered to the patient in one 24 hour period, regardless of whether the protocol calls for a once-daily, twice-daily, or thrice-daily administration of the drug. Thus, the total amount of drug is summed for a given 24 hour period to determine how much total drug the patient is to be administered in a given day. It is to be understood, however, that the amount of a drug to be administered to a particular patient will vary due to the extent of the patient's symptoms requiring treatment, the patient's tolerance for levodopa and/or carbidopa or drugs in general, the size of the patient, and various other factors that one of ordinary skill in the art must take into consideration.

The term "asymmetric dose" refers to the administration of more than one unequal doses of a particular drug in a 24 hour period. For example, two asymmetric doses of a particular drug are administered in a 24 hour period. Asymmetric doses are typically administered as a small dose in the morning and a proportionally larger dose in the evening.

"Titration" is the process of ramping up the total daily amount of drug administered to the patient. "Titration" allows the patient's body to get used to the higher dose, and ensures that the patient is prepared for subsequent higher doses of the drug through a succession of daily doses that are of increasing amount.

"Weaning," which is also referred to as "tapering," is the process of reducing the daily total dose a patient is receiving from the maintenance dose to a lesser dose. "Weaning" occurs when a patient is experiencing fewer of the symptoms requiring treatment or the treating physician would like to test whether the patient can reduce a maintenance dose. Weaning is effectively the opposite of titration, and occurs by successively reducing a daily maintenance dose to a lower level. Weaning can occur down to 0 mg of drug, depending on whether the patient is in fact ready to completely stop taking the medication.

"Maintenance" is the dosage amount that the patient needs to reach and maintain a desired level of relief from the symptoms under treatment. The maintenance dose is generally titrated to and maintained for a designated period of time. As discussed above, maintenance doses may also be diminished by weaning. As is known by those of ordinary skill in the art, maintenance doses should be set to minimize any side effects of the drug.

"Delayed release" dosage forms are a category of modified release dosage forms in which the release of the drug is delayed after oral administration for a finite period of time after which release of the drug is unhindered. Delayed release dosage forms are frequently used to protect an acid-labile drug from the low pH of the stomach or where appropriate to target the GI tract for local effect while minimizing systemic exposure. Enteric coating is frequently used to manufacture delayed release dosage forms.

The terms "sustained release," and "extended release" are used interchangeably herein to refer to a dosage form that provides for gradual release of a drug over an extended period of time. With extended release dosage forms, the rate of release of the drug from the dosage form is reduced in order to maintain therapeutic activity of the drug for a longer period of time or to reduce any toxic effects associated with a particular dosing of the drug. Extended release dosage forms have the advantage of providing patients with a dosing regimen that allows for less frequent dosing, thus enhancing compliance. Extended release dosage forms can also reduce peak-related side effects associated with some drugs and can maintain therapeutic concentrations throughout the dosing period thus avoiding periods of insufficient therapeutic plasma concentrations between doses.

The term "modified release" refers to a dosage form that includes both delayed and extended release drug products. The manufacture of delayed, extended, and modified release dosage forms are known to ordinary skill in the art and include the formulation of the dosage forms with excipients or combinations of excipients necessary to produce the desired active agent release profile for the dosage form.

The "gastric retentive" oral dosage forms described herein are a type of extended release dosage form. Gastric retentive dosage forms are beneficial for the delivery of drugs with reduced absorption in the lower GI tract or for local treatment of diseases of the stomach or upper GI tract. For example, in certain embodiments of gastric retentive oral dosage forms of the present invention, the dosage form swells in the gastric cavity and is retained in the gastric cavity of a patient in the fed med so that the drug may be released for heightened therapeutic effect. See, Hou et al., Crit. Rev. Ther. Drug Carrier Syst. 20(6):459-497 (2003).

The term "half-life" is a pharmacokinetic term used to indicate the length of time necessary to eliminate 50% of the remaining amount of drug present in the body.

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUG is directly proportional to the total amount of unaltered drug in the patient's blood plasma.

For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear AUC versus dose curve indicates rapid release of drug such that some of the drug is not absorbed, or the drug is metabolized before entering the blood stream.

The term "$C_{max}$" (i.e., "maximum concentration") is a pharmacokinetic term used to indicate the peak concentration of a particular drug in the blood plasma of a patient.

The term "$T_{max}$" (i.e., "time of maximum concentration" or "time of $C_{max}$") is a pharmacokinetic term used to indicate the time at which the $C_{max}$ is observed during the time course of a drug administration. As would be expected, a dosage form that would include an immediate release as well as a gastric retentive component would have a $T_{max}$ that is higher than the $C_{max}$ for an immediate release dosage form, but lower than the $T_{max}$ for a purely gastric retentive dosage form.

"Preventing," in reference to a disorder or unwanted physiological event in a patient, refers specifically to inhibiting or significant reducing the occurrence of symptoms associated with the disorder and/or the underlying cause of the symptoms.

"Treating," "treat," and "treatment" refer to reduction in severity and/or frequency of symptoms, elimination of symptoms and/or underlying cause, prevention of the occurrence of symptoms and/or their underlying cause, and improvement or remediation of damage.

The term "soluble" as used herein refers to a drug having an aqueous solubility (measured in water at 20° C.) greater than 10%, preferably greater than 20%, by weight. The terms "slightly soluble" and "sparingly soluble" refer to a drug having an aqueous solubility (measured at 20° C.) in the range of 2% to 10% by weight, while drugs having an aqueous solubility in the range of 0.001% to less than 2% by weight are referred to as "substantially insoluble."

The terms "hydrophilic" and "hydrophobic" are generally defined in terms of a partition coefficient P, which is the ratio of the equilibrium concentration of a compound in an organic phase to that in an aqueous phase. A hydrophilic compound has a P value less than 1.0, typically less than about 0.5, where P is the partition coefficient of the compound between octanol and water, while hydrophobic compounds will generally have a P greater than about 1.0, typically greater than about 5.0. The polymeric carriers herein are hydrophilic, and thus compatible with aqueous fluids such as those present in the human body.

The term "polymer" as used herein refers to a molecule containing a plurality of covalently attached monomer units, and includes branched, dendrimeric, and star polymers as well as linear polymers. The term also includes both homopolymers and copolymers, e.g., random copolymers, block copolymers and graft copolymers, as well as uncrosslinked polymers and slightly to moderately to substantially crosslinked polymers, as well as two or more interpenetrating cross-linked networks.

The term "vesicle" as used herein refers to a small (e.g., 0.01 to 1.0 mm), usually spherical structure that may contain or be composed of either lipoidal or aqueous material, or both. Suitable vesicles include, but are not limited to, liposomes, nanoparticles, and microspheres composed of amino acids. While vesicles are usually membrane-bound, they need not necessarily be membrane bound and within the context of the present invention, the term "vesicle" includes both membrane-bound and non-membrane-bound structures.

The terms "swellable" and "bioerodible" (or simply "erodible") are used to refer to the polymers used in the present dosage forms, with "swellable" polymers being those that are capable of absorbing water and physically swelling as a result, with the extent to which a polymer can swell being determined by the molecular weight or degree of crosslinking (for crosslinked polymers), and "bioerodible" or "erodible" polymers referring to polymers that slowly dissolve and/or gradually hydrolyze in an aqueous fluid, and/or that physically disentangle or undergo chemical degradation of the chains themselves, as a result of movement within the stomach or GI tract.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions in a USP Type II apparatus and immersed in 900 ml of simulated intestinal fluid (SIF) at pH 6.8 and equilibrated in a constant temperature water bath at 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The in vivo "release rate" and in vivo "release profile" refer to the time it takes for the orally administered dosage form, or the active agent-containing layer of a bilayer or multilayer tablet (administered when the stomach is in the fed mode) or the content of the active ingredient to be reduced to 0-10%, preferably 0-5%, of its original size or level, as may be observed visually using NMR shift reagents or paramagnetic species, radio-opaque species or markers, or radiolabels, or determined mathematically, such as deconvolution, upon its plasma concentration profiles.

The term "fed mode," as used herein, refers to a state which is typically induced in a patient by the presence of food in the stomach, the food-giving rise to two signals, one that is said to stem from stomach distension and the other a chemical signal based on food in the stomach. It has been determined that once the fed mode has been induced, larger particles are retained in the stomach for a longer period of time than smaller particles; thus, the fed mode is typically induced in a patient by the presence of food in the stomach. The fed mode is initiated by nutritive materials entering the stomach upon the ingestion of food. Initiation is accompanied by a rapid and profound change in the motor pattern of the upper GI tract, over a period of 30 seconds to one minute. The change is observed almost simultaneously at all sites along the G.I. tract and occurs before the stomach contents have reached the distal small intestine. Once the fed mode is established, the stomach generates 3-4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

The terms "subject," "individual" or "patient" are used interchangeably herein and refer to a vertebrate, preferably a mammal. Mammals include, but are not limited to, humans.

The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of formulation abraded or chipped is calculated. The friability of the tablets, of the present invention, is preferably in the range of about 0% to 3%, and values about 1%, or less, are considered acceptable for most drug and food tablet contexts. Friability which approaches 0% is particularly preferred.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

The term "bulk density," as used herein, refers to a property of powders and is defined as the mass of many particles of the material divided by the total volume they occupy. The total volume includes particle volume, interparticle void volume and internal pore volume.

The term "capping," as used herein, refers to the partial or complete separation of top or bottom crowns of the tablet main body. For multilayer tablets, capping refers to separation of a portion of an individual layer within the multilayer tablet. Unintended separation of layers within a multilayer tablet prior to administration is referred to herein as "splitting."

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the present disclosure or its claims.

Exemplary Dosage Forms

Described herein is a pharmaceutical oral dosage form comprising levodopa and carbidopa dispersed in a polymer matrix that, upon oral administration, swells dimensionally unrestrained, with the imbibition of fluid to a size sufficient for gastric retention in a stomach of a subject in a fed mode. The controlled-release oral dosage form allows effective treatment with oral administration once, twice or three times daily and may be used for the treatment of a movement disorder in a subject.

Levodopa, MSD, an aromatic amino acid, is a white, crystalline compound, slightly soluble in water, with a molecular weight of 197.2. It is designated chemically as (−)-L-alpha-amino-beta-(3,4-dihydroxybenzene) propanoic acid. Its empirical formula is $C_3H_{11}NO_4$ and its structural formula is:

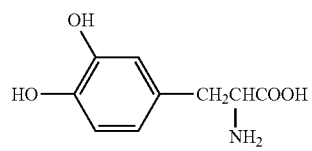

Carbidopa, MSD, an inhibitor of aromatic amino acid decarboxylase, is a white, crystalline compound, slightly soluble in water, with a molecular weight of about 244.3. It is designated chemically as (−)-L-alpha-hydrazino-alpha-methyl-beta-(3,4-dihydroxybenzene) propanoic acid monohydrate. Its empirical formula is $C_{10}H_{14}N_2O_4 \cdot H_2O$ and its structural formula is:

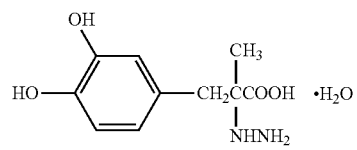

Tablet content is expressed in terms of anhydrous carbidopa, which has a molecular weight of 226.3.

It has been surprisingly discovered that a pharmaceutically acceptable gastric retentive dosage form can be formulated to provide release, in the upper gastrointestinal tract, of a combination of levodopa and carbidopa over an extended period of time such that oral administration of the dosage form once or twice daily is effective for treatment of a movement disorder.

In one embodiment, a first dose of levodopa and carbidopa is present in a gastric retentive extended release dosage form, wherein the levodopa and carbidopa are dispersed in a polymer matrix that, upon oral administration, swells dimensionally unrestrained with the imbibition of fluid, to a size sufficient for gastric retention in a stomach of a subject in a fed mode. In addition, the polymer matrix becomes slippery, which provides resistance to peristalsis and further promotes gastric retention. In the presently described dosage form, the levodopa and carbidopa may be released from the dosage form at least in part through erosion.

The combination of levodopa and carbidopa in the dosage form may vary, but typically range in ratios of levodopa to carbidopa of about 10:1 to about 2:1, and preferably about 4:1 or about 3:1 in the dosage form. Furthermore, the rate of levodopa drug release may be proportional to that of the carbidopa. The rate of release may occur over a period of 3, 4, 5, 6, 7, 8, 9, 10, 11, 12 hours or more.

The resulting dosage form has the unexpected property of maintaining levels of levodopa and carbidopa in the blood over extended periods of time, for example, 8 hours, 10 hours, or 12 hours, which are effective in treating CNS disorders including movement disorders.

The full dose of levodopa and carbidopa will typically be released from the dosage form during an extended period of time, for about 3 hours to about 12 hours, preferably about 6 hours to about 8 hours, to the to the upper gastrointestinal ("GI") tract, allowing a continuous flow of the drugs to the proximal region of the small intestine where levodopa is best absorbed.

The dosage forms disclosed herein are designed to be administered to a subject in a fed mode, as the dosage forms are designed to swell to a size which is large enough to be retained in a stomach in a fed mode. Such retention allows a prolonged release of active agent into the stomach.

In the normal digestive process, the passage of matter through the stomach is delayed by a physiological condition that is variously referred to as the digestive mode, the postprandial mode, or the "fed mode." Between fed modes, the stomach is in the interdigestive or "fasting" mode. The difference between the two modes lies in the pattern of gastroduodenal motor activity.

In the fasting mode, the stomach exhibits a cyclic activity called the interdigestive migrating motor complex ("IMMC"). This activity occurs in four phases:

Phase I, which lasts 45 to 60 minutes, is the most quiescent, with the stomach experiencing few or no contractions;

Phase II, characterized by sweeping contractions occurring in an irregular intermittent pattern and gradually increasing in magnitude;

Phase III, consisting of intense bursts of peristaltic waves in both the stomach and the small bowel, lasting for about 5 to 15 minutes; and Phase IV is a transition period of decreasing activity which lasts until the next cycle begins.

The total cycle time for all four phases is approximately 90 minutes. The greatest activity occurs in Phase III, when powerful peristaltic waves sweep the swallowed saliva, gastric secretions, food particles, and particulate debris, out of the stomach and into the small intestine and colon. Phase III thus serves as an intestinal housekeeper, preparing the upper tract for the next meal and preventing bacterial overgrowth.

The fed mode is initiated by nutritive materials entering the stomach upon the ingestion of food. Initiation is accompanied by a rapid and profound change in the motor pattern of the upper gastrointestinal tract, over a period of 30 seconds to one minute. The change is observed almost simultaneously at all sites along the G.I. tract and occurs before the stomach contents have reached the distal small intestine. Once the fed mode is established, the stomach generates 3-4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

Gastric retentive dosage forms described herein typically contain at least one hydrophilic polymer in a water-swellable polymer matrix having at least one drug dispersed therein. The polymer matrix, where in the at least one drug is dispersed absorbs water, causing the matrix to swell, which in turn promotes retention of the dosage form in the upper gastrointestinal tract (GI) of a subject. In addition, the matrices become slippery, which provides resistance to peristalsis and further promotes gastric retention.

With the dosage forms described herein, the rate at which the drugs are released by the extended release layer into the gastrointestinal tract is largely dependent on the rate at and the degree to which the polymer matrix swells. The polymer used in the dosage forms of the present invention should not release the drug at too rapid a rate so as to result in a drug overdose or rapid passage into and through the gastrointestinal tract, nor should the polymer release drug too slowly to achieve the desired biological effect. Thus, polymers that permit a rate of drug release that achieves the requisite pharmacokinetics for both the levodopa and the carbidopa for a desired duration, as may be determined using a USP Disintegration Test or Dissolution Test, are determined for use in the dosage forms described herein.

Polymers suitable for use in the dosage forms described herein include those that both swell upon absorption of gastric fluid and gradually erode over a time period of hours. Upon swelling of the polymer matrix, soluble drugs dispersed in the matrix will slowly dissolve in the permeating fluid and diffuse out from the matrix. Drugs that are poorly, or sparingly, soluble are released primarily via erosion of the polymer matrix. Both levodopa and carbidopa are poorly soluble in aqueous media. Erosion initiates simultaneously with the swelling process, upon contact of the surface of the dosage form with gastric fluid. Erosion reflects the dissolution of the polymer beyond the polymer gel-solution interface where the polymer has become sufficiently dilute that it can be transported away from the dosage form by diffusion or convection. This may also depend on the hydrodynamic and mechanical forces present in the gastrointestinal tract during the digestive process. While swelling and erosion occur at the same time, it is preferred herein that drug release should be erosion-controlled, meaning that the selected polymer should be such that complete drug release occurs primarily as a result of erosion rather than swelling and dissolution. However, swelling should take place at a rate that is sufficiently fast to allow the tablet to be retained in the stomach. At minimum, for an erosional gastric retentive dosage form, there should be an extended period during which the dosage form maintains its size before it is diminished by erosion. Furthermore, the polymer which imbibes fluid to form a gastric retained, extended release polymer matrix is any polymer that is non-toxic, that swells in a dimensionally unrestricted manner upon imbibition of water, and that provides for sustained release of at least one incorporated drug.

Water-swellable, erodible polymers suitable for use herein are those that swell in a dimensionally unrestrained manner upon contact with water, and gradually erode over time. Examples of such polymers include cellulose polymers and their derivatives including, but not limited to, hydroxyalkyl celluloses, hydroxymethyl cellulose, hydroxyethyl cellulose, hydroxypropyl cellulose, hydroxypropylmethyl cellulose, carboxymethylcellulose, microcrystalline cellulose; polysaccharides and their derivatives; polyalkylene oxides, such as polyethylene glycols, particularly high molecular weight polyethylene glycols; chitosan; poly(vinyl alcohol); xanthan gum; maleic anhydride copolymers; poly(vinyl pyrrolidone); starch and starch-based polymers; maltodextrins; poly(2-ethyl-2-oxazoline); poly(ethyleneimine); polyurethane; hydrogels; crosslinked polyacrylic acids; and combinations or blends of any of the foregoing.

Further examples are copolymers, including block copolymers and graft polymers. Specific examples of copolymers are PLURONIC® and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

Preferred swellable, erodible hydrophilic polymers suitable for forming the gastric retentive portion of the dosage forms described herein are poly(ethylene oxide), hydroxypropyl methyl cellulose, and combinations of poly(ethylene oxide) and hydroxypropyl methyl cellulose. Polyethylene oxide) is used herein to refer to a linear polymer of unsubstituted ethylene oxide. The molecular weight of the poly (ethylene oxide) polymers can range from about $9 \times 10^5$ Daltons to about $8 \times 10^6$ Daltons. A preferred molecular weight poly(ethylene oxide) polymer is about $5 \times 10^5$ Daltons and is commercially available from The Dow Chemical Company (Midland, Mich.) referred to as SENTRY® POLYOX® water-soluble resins, NF (National Formulary) grade WSR Coagulant. The viscosity of a 1% water solution of the polymer at 25° C. preferably ranges from 4500 to 7500 centipoise. In terms of their viscosities, one class of preferred alkyl-substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C.

The amount of polymer relative to the drug can vary, depending on the drug release rate desired and on the polymer, its molecular weight, and excipients that may be present in the formulation. The amount of polymer in the extended release portion will be sufficient however to retain at least about 50% of the drugs within the matrix one hour after ingestion (or immersion in the gastric fluid). Preferably, the amount of polymer is such that at least 55%, 60%, 65%, 70%, 75%, or 80% of the drugs remains in the extended release matrix one hour after ingestion. The amount of polymer is such that at least about 20%, 25%, 30%, 35%, 40%, 45%, 50%, 55% or 60% of the drugs remains in the extended release matrix four hours after ingestion. The amount of polymer is such that at least about 60%, 65%, 70%, 75%, 80%, or 85% of the drugs is released within six hours after ingestion. In all cases, however, the drugs will be substantially all released from the matrix within about eight, nine, or ten hours, and preferably within about eight hours after ingestion, and the polymeric matrix will remain substantially intact until all of the drug is released. The term "substantially intact" is used herein to denote a polymeric matrix in which the polymer portion substantially retains its size and shape without deterioration due to becoming solubilized in the gastric fluid or due to breakage into fragments or small particles.

The water-swellable polymers can be used individually or in combination. Certain combinations will often provide a more controlled release of the drug than their components when used individually.

As discussed above, the gastric retentive nature and release profiles of a dosage form will depend partially upon the molecular weight of the swellable polymer. The polymers are preferably of a moderate to high molecular weight (300,000 Da to 12,000,000 Da) to enhance swelling and provide control of the release of the levodopa and carbidopa via erosion of the polymer matrix. An example of suitable poly(ethylene oxide) polymers are those having molecular weights (viscosity average) on the order of 900,000 Da to 2,000,000 Da. Using a lower molecular weight ("MW") polyethylene oxide, such as POLYOX™ 1105 (900,000 MW) release for both drugs are higher. Using a higher molecular weight polyethylene oxide (such as POLYOX™ N-60K (2,000,000 MW) or POLYOX™ WSR-301 (4,000,000 MW) reduces the rate of release for both drugs. In one embodiment of the invention, a hydroxypropylmethylcellulose polymer of such molecular weight is utilized so that the viscosity of a 1% aqueous solution at about 20° C. is about 4000 cps to greater than 100,000 cps.

The gastric retentive dosage form or the extended release portion of a gastric retentive dosage form may comprise a range of hydrophilic swellable polymers both in terms of type, approximate molecular weight and weight percent. For example, a gastric retentive dosage form may be formulated to comprise about 5 wt % to about 70 wt % hydrophilic polymer. In another embodiment, the at least one hydrophilic polymer is present in the dosage form in an amount ranging from about 15 wt % to about 65 wt %. In yet another embodiment, the at least one hydrophilic polymer is present in the dosage form in an amount ranging from about 20 wt % to about 60 wt %. In still another embodiment, the at least one hydrophilic polymer is present in the dosage form in an amount ranging from about 30 wt % to about 50 wt %. In still another embodiment, the at least one hydrophilic polymer is present in the dosage form in about 20 wt %, 25 wt %, 30 wt %, 35 wt %, 40 wt %, 45 wt %, 50 wt %, 55 wt %, or 60 wt %.

Combinations of different poly(ethylene oxide)s are also contemplated, with polymers of different molecular weights contributing to different dosage form characteristics. For example, a very high molecular weight poly(ethylene oxide) such as POLYOX™ 303 (with a number average molecular weight of 7 million) or POLYOX™ Coag (with a number average molecular weight of 5 million) may be used to significantly enhance diffusion relative to disintegration release by providing high swelling as well as tablet integrity. Incorporating a lower molecular weight poly(ethylene oxide) such as POLYOX™ WSR N-60K (number average molecular weight approximately 2 million) with POLYOX™ 303 and/or POLYOX™ Coag increases disintegration rate relative to diffusion rate, as the lower molecular weight polymer reduces swelling and acts as an effective tablet disintegrant. Incorporating an even lower molecular weight poly(ethylene oxide) such as POLYOX™ WSR N-80 (number average molecular weight approximately 200,000) further increases disintegration rate. Alternatively, incorporating a poly(ethylene oxide) such as POLYOX™ WSR N-60K (number average molecular weight approximately 2 million) with an even lower molecular poly(ethylene oxide) such as POLYOX™ N-1105 (number average molecular weight approximately 900,000 Da) may provide extended release of the drugs in the swelling dosage form which erodes in a way to provide the desired release rate.

Hydrophilic polymers as described above are added to a gastric retentive dosage form to provide swelling to an extent that will promote retention in a stomach in a fed mode. A typical dosage form may swell to approximately 115% of its original volume within 30 minutes after administration, and at a later time may swell to a volume that is 130%, 140%, 150%, 160%, 170% or more of the original volume of the dosage form prior to imbibition of fluid.

Dosage forms prepared for oral administration according to the present disclosure will generally contain other inactive additives (excipients) such as binders, lubricants, disintegrants, fillers, stabilizers, surfactants, coloring agents, and the like.

Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., *acacia* sodium alginate, polyvinylpyrrolidone (PVP), cellulosic polymers (including hydroxypropyl cellulose (HPC), hydroxypropyl methylcellulose, methyl cellulose, microcrystalline cellulose, ethyl cellulose, hydroxyethyl cellulose, and the like), and Veegum.

In one embodiment, the GR dosage form comprises a binder that is present in an amount ranging from about 0.1 wt % to about 20 wt % or in an amount ranging from about 2 wt % to about 15 wt %, or in an amount ranging from about 2 wt % to about 8 wt %. In another embodiment, the GR dosage form comprises a binder that is present in an amount that is about 1.0 wt %, 1.1 wt %, 1.2 wt % 1.4 wt %, 1.5 wt %, 1.7 wt %, 1.8 wt %, 1.9 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt % or 8.0 wt % of the dosage form.

Fillers include, for example, materials such as silicon dioxide, titanium dioxide, alumina, talc, kaolin, powdered cellulose, and microcrystalline cellulose, as well as soluble materials such as mannitol, urea, sucrose, lactose, lactose monohydrate, dextrose, sodium chloride, and sorbitol. Solubility-enhancers, including solubilizers per se, emulsifiers, and complexing agents (e.g., cyclodextrins), may also be advantageously included in the present formulations. In one embodiment, the filler is microcrystalline cellulose (MCC) or mannitol or a mixture of and mannitol. (MCC) and/or mannitol. In another embodiment, a GR dosage form comprises about 35 wt % to about 85 wt %, about 45 wt % to about 75 wt %, about 50 wt % to about 65 wt % filler. In another embodiment, the GR dosage form comprises a filler that is present in an amount that is about 45 wt %, 50 wt %, 51 wt %, 52 wt %, 53 wt %, 55 wt %, 60 wt %, 65 wt %, 68 wt %, 68 wt %, 70 wt %, 71 wt %, 72 wt %, 75 wt %, 80 wt %, or 85 wt % of the dosage form.

Lubricants are used to facilitate tablet manufacture, promoting powder flow and preventing particle capping (i.e., particle breakage) when pressure is relieved. Useful lubricants are magnesium stearate (in a concentration of from 0.25 wt % to 3 wt %, preferably 0.2 wt % to 1.0 wt %, more preferably about 0.5 wt %), calcium stearate, stearic acid, and hydrogenated vegetable oil (preferably comprised of hydrogenated and refined triglycerides of stearic and palmitic acids at about 1 wt % to 5 wt %, most preferably less than about 2 wt %). Solubility-enhancers, including solubilizers per se, emulsifiers, and complexing agents (e.g., cyclodextrins), may also be advantageously included in the present formulations. Stabilizers, as well known in the art, are used to inhibit or retard drug decomposition reactions that include, by way of example, oxidative reactions.

The formulations are typically in the form of tablets. Other formulations contain the matrix/active agent particles in capsules. The encapsulating material should be highly soluble so that the particles are freed and rapidly dispersed in the stomach after the capsule is ingested. Such dosage forms are prepared using conventional methods known to those in the field of pharmaceutical formulation and described in the pertinent texts, e.g., in Gennaro, A. R., editor. "Remington: The Science & Practice of Pharmacy", 21st ed., Williams & Williams, and in the "Physician's Desk Reference", 2006, Thomson Healthcare.

The tablets described herein may have individual layers, each containing levodopa and carbidopa, for delivering the component drug(s) in the immediate release or the extended release mode. For example, a layer for immediate release of levodopa and carbidopa can be added to a layer containing both drugs for extended release.

Alternative gastric retentive drug delivery systems include the swellable bilayer described by Franz, et al., U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389, and Shell, et al., WO 9855107, and the pulsatile gastric retentive dosage form by Cowles et al., U.S. Pub. No. 2009/0028941, all of which are incorporated herein by reference.

In a preferred embodiment, the gastric retentive dosage form comprises an extended release component (ER layer or portion) and an immediate release component (IR layer or portion). The ER component comprises the at least one hydrophilic polymer in a water-swellable polymer matrix which swells upon imbibition of fluid to a size large enough to promote gastric retention. Both the extended release and immediate release components contain levodopa and carbidopa.

In one embodiment, the dosage form is a bilayer tablet comprising an immediate release layer and an extended release layer. Bilayer tablets are known in the art, and the skilled artisan will be capable of their preparation using the methods disclosed herein along with commonly available methods.

In one embodiment, the immediate release portion comprises levodopa and carbidopa at lower amounts as compared to the amounts of levodopa and carbidopa in the extended release layer of the dosage form. In another aspect, the amount of levodopa in the immediate release portion is generally between about 2 to 5, more typically between 3 to 4 times the amount of carbidopa in the immediate release portion. In one embodiment, the ratio levodopa to carbidopa in the immediate release portion is about 3:1. In a preferred embodiment, the ratio of levodopa to carbidopa in the immediate release portion is about 3:1.

In a preferred aspect, the immediate release portion is in contact with the extended release portion.

An optional sub-coat layer may be employed when it is desirable to protect the drug in the drug layer from a component in a protective layer. For example, a protective layer that serves as an enteric coating may comprise an acidic component, and the optional sub-coat would be included to protect the drug from such an acidic component. The sub-coat layer should allow for relatively immediate release of the drug layer once the protective layer is removed. Examples of suitable materials for the sub-coat layer may include, for example, OPADRY® YS-1-10699, OPADRY® YS-1-19025-A-Clear and OPADRY-03K (supplied by Colorcon, Pa.). The sub-coat layer may also contain additional excipients, including any described elsewhere herein, as well as alkaline compounds such as bases, salts, and the like. The thickness of the sub-coat layer is typically determined by the manufacturing process percentage weight gain specification but can be, for example, within the range of about 10-50 μm.

The immediate release portion may further comprise excipients such as binders, lubricants, disintegrants, superdisintegrants, fillers, stabilizers, surfactants, coloring agents, and the like, as described above for the extended release component. In some embodiments, the binder within the immediate release portion is hydroxypropylcellulose (e.g., Klucel E) or polyvinylpyrrolidone. The binder in the immediate release layer may be present in an amount ranging from about 0-20 wt %.

Disintegrants or superdisintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). In some embodiments, the superdisintegrant is croscarmellose sodium (Ac-Di-Sol®) and is present in an amount ranging from about 0.5 wt % to about 10 wt %. The disintegrant or superdisintegrant may be present in the immediate release component in an amount ranging from about 0.5 wt % to about 2 wt %, or may be present is an amount approximating 0.5 wt %, 1.0 wt %, 1.5 wt %, 2.0 wt %, 2.5 wt %, 3.0 wt %, 4.0 wt %, 5.0 wt %, 6.0 wt %, 7.0 wt %, 8.0 wt %, 9.0 wt % or 10.0 wt %.

In one embodiment, the disintegrant or superdisintegrant is sprayed onto the granulation mixture during granulation. In another embodiment, the disintegrant or super disintegrant is added to the active granules during blending of the granules with the additional fillers and/or excipients. In yet another embodiment, the disintegrant or superdisintegrant is added to the active granules both during granulation and during blending of the active granules with excipients.

The immediate release portion may release at least 80-100% of the active agents within the first hour, first 30 minutes, or first 15 minutes after oral administration. Administration to the subject of a dosage form comprising the immediate release portion may provide a fast onset plasma level of levodopa sufficient to provide therapeutic efficacy to the subject. In one embodiment, the efficacious threshold for treatment of Parkinson's Disease is about 300 ng/mi. In another embodiment, administration to a subject of a dosage form comprising the immediate release portion provides a plasma level of levodopa of at least about 300 nm/ml within about 30 minutes, 45 minutes, 60 minutes, 90 minutes or 2 hours after administration of the dosage form.

Is it understood by the skilled artisan that delivery time or duration of drug release by a particular dosage form is distinct from the duration of drug delivery by the dosage form. As an example, while an extended release dosage form may release one or more drugs over a period of 3, 4 or more hours, depending on the half-life of the drug and the time of transit of that drug through the gastrointestinal tract, the relevant sites of absorption will be exposed for a period of time beyond the time of drug release from the dosage form. Thus, for example, a dosage form that releases one or more drugs over a period of approximately 8 hours may be providing delivery of that drug for a period of approximately 12 hours.

The dosage form, as presently described, possesses the additional advantageous feature of being formulated as a standard oral dosage size, then after administration, imbibing water from the gastric fluid and swelling to a size large enough to be retained in the stomach in a fed mode. This is particularly important for subjects who experience difficulty in swallowing, such as subjects suffering from Parkinson's Disease.

Other alternatives for incorporating the immediate release pulse with the delayed release pulse will be apparent to those of skill in the art upon consideration of this disclosure.

Dosage forms that provide more than two pulses of drug release are contemplated, and a skilled artisan will appreciate the modifications to the dosage forms described above to provide a third, fourth or further drug dose pulse. Multiple pulses are possible using variations of the embodiments described herein. For dosage forms using erodible inserts, a plurality of pulses may be obtained by using more than two identical or different erodible inserts in the dosage form, in which the different inserts provide different erosion times. For dosage forms comprising tablet cores and/or beads, additional pulses may be obtained by using a plurality of gastric retentive layers alternated with layers comprising the active agent.

For any of the embodiments, the optional initial (i.e., immediate release) pulse of drug can be combined with the delayed release pulse in any suitable manner. In general, the initial pulse of drug is released in the stomach rapidly upon administration. The second (i.e., delayed) pulse of active agent may be prepared such that it follows administration of the dosage form at any time, and the skilled artisan will understand in view of the disclosure herein how to provide the desired time of release. For example, increasing the thickness of the walls of the gastric retentive insert will increase the time delay between administration of the dosage form and release of the delayed pulse of drug. The optimal time delay between administration of the dosage form and release of the delayed pulse will depend on a number of factors, such as the condition being treated, the physical characteristics and daily routine of the patient being treated, and the like. Additional details of such pulsatile dosage forms are described in U.S. Patent Publication No. 2009/0028941 (herein incorporated by reference).

In various embodiments, the delayed pulse will release active agent to the duodenum and/or the small intestine of the patient within about 2 to 12 hours after administration of the dosage form, for example within about 3 to 9 hours, or for example within about 4 hours to 8 hours. Release of the delayed release pulse may be targeted for about 3 hours, 4 hours, 5 hours, 6 hours, 7 hours, 8 hours, 9 hours, 10 hours, 11 hours, or 12 hours after administration of the dosage form. As a further example, release of the delayed release pulse may be target for between about 2 hours to 4 hours, or between about 3 hours to 5 hours, or between about 5 hours to 7 hours, or between about 6 hours to 8 hours after administration of the dosage form.

Generally, the initial pulse (when present) releases a dose of active agent or drug that is between about 0.25 and 20 times the dose of active agent or drug that is present in the delayed pulse. Measured as a ratio, the drug dose ratio of the initial to delayed pulses may be about 0.25 to 4, or 0.5 to 2, or 0.75 to 1.25, and can be 1 to 1. The amount of active agent in the formulation typically ranges from about 0.05 wt % to about 95 wt % based on the total weight of the formulation. For example, the amount of active agent may range from about 0.05 wt % to about 50 wt %, or from about 0.1 wt % to about 25 wt %, or from about 1 wt % to about 15 wt %. Alternatively, the amount of active agent in the formulation may be measured so as to achieve a desired dose, concentration, plasma level upon administration, or the like. The amount of active agent may be calculated to achieve a specific dose (i.e., unit weight of active agent per unit weight of patient) of active agent. Furthermore, the treatment regimen may be designed to sustain a predetermined systemic level of active agent. For example, formulations and treatment regimen may be designed to provide an amount of active agent that ranges from about 0.001 mg/kg/day to about 100 mg/kg/day for an adult. One of skill in the art will appreciate that dosages may vary depending on a variety of factors, including physical characteristics of the patient and duration of treatment regimen.

Numerous materials useful for manufacturing dosage forms described herein are described in *Remington: The Science and Practice of Pharmacy*, 20$^{th}$ edition (Lippincott Williams & Wilkins, 2000) and Ansel et al., *Pharmaceutical Dosage Forms and Drug Delivery Systems*, 6$^{th}$ Ed. (Media, Pa.: Williams & Wilkins, 1995). Pharmaceutically acceptable additives or excipients include binders (e.g., ethyl cellulose, gelatin, gums, polyethylene glycol, polyvinylpyrrolidone, polyvinylalcohol, starch, sugars, waxes), disintegrants, coloring agents, diluents (e.g., calcium sulfate, cellulose, dicalcium phosphate, kaolin, lactose, mannitol, microcrystalline cellulose, sodium chloride, sorbitol, starch, sucrose), flavoring agents, glidants (e.g., colloidal silicon dioxide, talc), and lubricants (e.g., calcium stearate, glyceryl behenate, hydrogenated vegetable oils, magnesium stearate, polyethylene glycol, sodium stearyl fumarate, stearic acid, stearyl behenate, talc), sweeteners, polymers, waxes, and solubility-retarding materials. The dosage forms described herein can be made by techniques that are well established in the art, including wet granulation, fluid-bed granulation, dry granulation, direct compression, and so forth.

A delayed pulse of drug released from the dosage forms is provided by incorporating the drug into a gastric-retentive matrix. If the drug to be administered is acid sensitive, then, as for the drug delivered in the initial pulse, the drug delivered in the delayed pulse is acid protected by using, for example, an enteric coating and/or is formulated with a base.

Various embodiments of dosage forms for delivery of levodopa and carbidopa are contemplated. In one embodiment, an immediate-release compartment comprising a blend of levodopa and/or carbidopa and one or more polymers is surrounded by an extended-release compartment. The extended release compartment is comprised of a hydrophilic polymer, and other components to provide the desirable release rate, such as a first order release which is interrupted after a period of extended drug release by a pulse of one or both drugs from the immediate-release compartment. In another embodiment, the dosage form comprises two separate immediate release compartments, with one or both drugs, and each immediate release compartment is surrounded or encased by a scored extended release compartment. The scored extended release compartment allows the dosage form to be separated into two individual portions, providing the option for a patient to take a smaller dose. In another embodiment, one or both of levodopa and carbidopa are incorporated into any of the dosage forms described herein in micronized form, optionally admixed with an inert particle or carrier. A micronized form of the drug can be incorporated into one or both of an immediate release compartment and an extended release compartment. A skilled artisan will appreciate that a dosage form with a plurality of layers, such as an immediate release compartment encased by an extended release compartment which is encased by a second immediate release compartment, is contemplated.

The dosage forms are intended for oral dosage administration. Preferred oral dosage forms include tablets, capsules, and the like. Tablets may comprise, for example, a flavored base such as compressed lactose, sucrose and *acacia* or tragacanth and an effective amount of an active agent. Tablets can be prepared by common tabletting methods that involve mixing, comminution, and fabrication steps commonly practiced by and well known to those skilled in the art of manufacturing drug formulations. Examples of such techniques are: (1) direct compression using appropriate punches and dies, typically fitted to a suitable rotary tabletting press; (2) injection or compression molding; (3) granulation by fluid bed, by low or high shear granulation, or by roller compaction, followed by compression; (4) extrusion of a paste into a mold or to an extrudate to be cut into lengths; (5) coating techniques, including pan-coating, fluid-bed coating and bottom spray methods (Wurster) and other film coating methods; and (6) powder layering.

When tablets are made by direct compression, the addition of lubricants may be helpful and is sometimes important to promote powder flow and to prevent breaking of the tablet when the pressure is relieved. Examples of typical lubricants are magnesium stearate (in a concentration of from 0.25% to 3% by weight, preferably about 1% or less by weight, in the powder mix), stearic acid (0.5% to 3% by weight), and hydrogenated vegetable oil (preferably hydrogenated and refined triglycerides of stearic and palmitic acids at about 1% to 5% by weight, most preferably about 2% by weight). Additional excipients may be added as granulating aids (low molecular weight HPMC at 2-5% by weight, for example), binders (microcrystalline cellulose, for example), and additives to enhance powder flowability, tablet hardness, and tablet friability and to reduce adherence to the die wall. Other fillers and binders include, but are not limited to, lactose (anhydrous or monohydrate), maltodextrins, sugars, starches, and other common pharmaceutical excipients. These additional excipients may constitute from 1% to 50% by weight, and in some cases more, of the tablet.

In one aspect, a method of making a gastric retentive extended-release dosage form as a single layer tablet comprising wet granulation levodopa and carbidopa with the binder is provided. The wet granulation can be a fluid-bed or high shear granulation method. The granulated particles are then blended with additional excipients as needed to form a mixture which is then compressed to form tablets.

Extended release polymer matrices comprising levodopa and carbidopa can be made using, for example, POLYOX™ 1105 (approximate molecular weight of 900,000 Daltons), POLYOX™ N-60K (approximate molecular weight of 2,000,000 Daltons), and/or POLYOX™ WSR-301 (approximate molecular weight of 4,000,000 Daltons). Additional polymers appropriate for use in formulating extended release polymer matrices are discussed in more detail above. Prior to compression, components can be granulated using a top spray fluid bed granulator After fluid bed granulation and drying of the resultant particles, batches are characterized with respect to properties such as final Loss on Drying (LOD), bulk density, tap density, and particle size.

Loss on Drying (LOD) is determined after each granulation using the Moisture Analyzer. One 1 gram (g) samples are taken and loaded into the moisture analyzer. The sample is run for 5 minutes at a temperature of 105° C.

Bulk and tap densities can be determined as follows. A graduated cylinder is filled with a certain amount of material (82-88 g), and the volume recorded to determine the material bulk density. Tap density can be determined with a help of a Tap Density Tester by exposing the material to 100 taps per test and recording the new volume.

Particle size determination is performed immediately after granulation, after sieving through 20 mesh screen to remove agglomerates. Particle diameter is determined with a sieve-type particle diameter distribution gauge using sieves with openings of 44, 53, 75, 106, 150, and 250 mesh. Fractions are weighed on Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

The granulated mixture can be blended with the polymer, filler and lubricant in a V-blender. The resultant mixture can be compressed into monolithic, single-layer tablets using a Manesty® BB4 press, with a modified oval tool. Tablets may be prepared at a rate, for example, of approximately 800 tablets per minute.

Tablets are then characterized with respect to disintegration and dissolution release profiles as well as tablet hardness, friability and content uniformity.

Dissolution profiles for the tablets are determined in a USP apparatus. For example, a USP Apparatus 1 (basket), run at 100 or 150 revolutions per minute (rpm), a USP Apparatus 2 (paddle), run at 100 or 150 rpm, or a USP Apparatus 3 (reciprocating cylinder) run at 10, 20, or 20 cycles per minute (cpm) or dips per minute (dpm). In all cases, the dissolution medium contains 0.1 N Hydrochloric acid (HCl), maintained at a temperature of 37±0.5° C. Cumulative drug release over time is represented as a percent of labeled claim (% LC) for drug content and is plotted as a function of dissolution medium sampling time. The resulting cumulative dissolution profiles for the tablets are based upon a theoretical percent active added to the formulations.

Tablet hardness changes rapidly after compression as the tablet cools. A tablet that is too hard may not break up and dissolve into solution before it passes through the body. In the case of the presently disclosed gastric retentive dosage forms, a tablet that is too hard may not be able to imbibe fluid rapidly enough to prevent passage through the pylorus in a stomach in a fed mode. A tablet that is too soft may break apart, not handle well, and can create other defects in manufacturing. A soft tablet may not package well or may not stay together in transit.

After tablets are formed by compression, it is desired that the tablets have a strength of at least 9 Kiloponds to 25 Kiloponds (Kp)/cm$^2$, preferably at least about 12 Kp to 20 (Kp)/cm$^2$. A hardness tester is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially important during any transport of the dosage form as any fracturing of the final dosage form will result in a subject receiving less than the prescribed medication. Friability can be determined using a Roche Friability Drum according to standard USP guidelines which specifies the number of samples, the total number of drum revolutions and the drum rpm to be used. Friability values of from 0.8% to 1.0% are regarded as constituting the upper limit of acceptability.

The prepared tablets are tested for content uniformity to determine if they meet the pharmaceutical requirement of <6% relative standard deviation (RSD). Each tablet is placed in a solution of 1.0 N HCl and stirred at room temperature until all fragments have visibly dissolved. The solution containing the dissolved tablet is analyzed by HPLC.

In addition to the foregoing components, it may be necessary or desirable in some cases (depending, for instance, on the particular composition or method of administration) to incorporate any of a variety of additives, e.g., components that improve drug delivery, shelf-life and patient acceptance. Suitable additives include acids, antioxidants, antimicrobials, buffers, colorants, crystal growth inhibitors, defoaming agents, diluents, emollients, fillers, flavorings, gelling agents, fragrances, lubricants, propellants, osmotic modifiers, thickeners, salts, solvents, surfactants, other chemical stabilizers, or mixtures thereof. Examples of these additives can be found, for example, in M. Ash and I. Ash, *Handbook of Pharmaceutical Additives* (Hampshire, England: Gower Publishing, 1995), the contents of which are herein incorporated by reference.

Guidance is provided herein for the administration of the dosage forms of the disclosure. It will be appreciated by the skilled artisan, however, that modifications to dosage, regimen, etc. may be required and is best determined by the practitioner on a patient-by-patient basis. The skilled practitioner will be capable of making such modifications based on commonly available knowledge. The dosage forms are typically employed for once-a-day oral administration.

The formulations described herein may be presented in unit dose form or in multi-dose containers with an optional preservative to increase shelf life. Also contemplated are kits for the treatment of any of the conditions described herein, or any of the conditions that may be treated using the dosage forms described herein. The kit comprises the dosage form in either a single unit container or a multiple unit container, and may further comprise instructions for dosage or administration, package inserts, and the like.

In another aspect, a method for treating a subject suffering from a movement disorder by oral administration of a gastric retentive extended release dosage form as described above is provided.

The method presently disclosed is useful for treating numerous movement disorders include, by way of illustration and not limitation, Parkinson's Disease, Restless Leg Syndrome (RLS), Huntington's chorea, progressive supranuclear palsy, Wilson's disease, Tourette's syndrome, epilepsy, tardive dyskinesia, and various chronic tremors, tics and dystonias.

Generally, the frequency of administration of a particular dosage form is determined to provide the most effective results in an efficient manner without overdosing and varies according to the following criteria: (1) the characteristics of the particular drug(s), including both its pharmacological characteristics and its physical characteristics, such as solubility; (2) the characteristics of the swellable matrix, such as its permeability; and (3) the relative amounts of the drug and polymer. In most cases, the dosage form is prepared such that effective results are achieved with administration once every eight hours, once every twelve hours, or once every twenty-four hours. As previously discussed, due to the physical constraints placed on a tablet or capsule that is to be swallowed by a patient, most dosage forms can only support a limited amount of drug within a single dosage unit.

In one embodiment, the dosage form allows a dosing frequency of two times a day (b.i.d.) or three times a day (t.i.d.) to result in sustained plasma concentration of levodopa or both levodopa and carbidopa as compared to current immediate or sustained release products which require more frequent administration for therapeutic efficacy.

Within the context of the present disclosure, the gastric retentive dosage forms have the advantage of improving patient compliance with administration protocols because the drugs may be administered in a once-daily or twice-daily dosing regimen, rather than the multiple dosing administrations necessary for currently available dosage forms of levodopa and carbidopa in order to maintain a desired level of relief. One embodiment of the invention relates to a method of administering a therapeutically effective amount of levodopa and carbidopa to a patient in need thereof, comprising administering levodopa and carbidopa or pharmaceutically acceptable salts thereof, in a gastric retentive dosage form once in the morning or evening in a once a day daily regime. Another embodiment comprises administering the gastric retentive dosage form twice a day, for example once in the morning and once in the evening in a twice a day daily dosage regime.

For all modes of administration, the gastric retentive dosage forms described herein are preferably administered in the fed mode, i.e., with or just after consumption of a small meal (see U.S. Publication No. 2003/0104062, herein incorporated by reference). When administered in the evening fed mode, the gastric retentive dosage form may provide the subject with continued relief from pain through the night and into the next day. The gastric retentive dosage form of the present invention is able to provide pain relief for an extended period of time because the dosage form allows for both extended release of the acetaminophen and opioid and the superior absorption of the drugs in the GI tract.

In some aspects, the postprandial or fed mode can also be induced pharmacologically, by the administration of pharmacological agents that have an effect that is the same or similar to that of a meal. These fed-mode inducing agents may be administered separately or they may be included in the dosage form as an ingredient dispersed in the shell, in both the shell and the core, or in an outer immediate release coating. Examples of pharmacological fed-mode inducing agents are disclosed in U.S. Pat. No. 7,405,238, entitled "Pharmacological Inducement of the Fed Mode for Enhanced Drug Administration to the Stomach," inventors Markey, Shell, and Berner, the contents of which are incorporated herein by reference.

It will be recognized by those of skill in the art that the methods of administration and dosage forms described herein are also suitable for therapeutic agents other than those previously mention, including drugs and active agents that are suitable for treatment of conditions other than CNS and related conditions. Such therapeutic agents include those commonly administered via the oral route, those where oral administration is desirable, and those that have not previously been administered via the oral route but that would benefit from delivery via the oral route using the methods and dosage forms described herein.

In one embodiment, the dosage forms described herein find use for drugs that have a reduced absorption in the lower GI tract and a reduced bioavailability due to first-pass metabolism. Sparingly soluble drugs particularly can suffer from both of these absorption issues, since hepatic metabolism tries to make these sparingly soluble drugs more polar to eliminate them vial renal clearance, and the drug's poor solubility makes the upper GI tract too short for adequate absorption. Any of the drugs in the examples listed below that are sparingly soluble are contemplated to benefit from administration in a dosage form as described herein.

Alternative active agents for use in the dosage forms described herein may include anti-microbial agents, anti-diabetic agents, analgesics, anti-inflammatory agents, anti-convulsant agents, CNS and respiratory stimulants, neuroleptic agents, hypnotic agents and sedatives, anxiolytics and tranquilizers, other anti-cancer drugs including antineoplastic agents, antihyperlipidemic agents, antihypertensive agents, cardiovascular preparations, anti-viral agents, sex steroids, muscarinic receptor agonists and antagonists, and macromolecular active agents such as DNA, RNA, proteins, and peptide drugs. Some examples of these active agents are provided below.

Analgesics useful in the dosage forms described herein include by way of example non-opioid analgesic agents such as apazone, etodolac, difenpiramide, indomethacin, meclofenamate, mefenamic acid, oxaprozin, phenylbutazone, piroxicam, and tolmetin; and opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol. Additional analgesic agents contemplated for use in the dosage forms described herein include non-steroidal anti-inflammatory agents (NSAIDs). Examples of suitable commercially available opioid analgesics useful in the dosage forms include PERCOCET® (oxycodone; Dupont Merck Pharmaceuticals, Wilmington, Del.), ULTRACET® (tramadol; Johnson & Johnson, New Brunswick, N.J.), and CLONOPIN™ (clonazepam; Hoffmann-LaRoche, Nutley, N.J.). It will be appreciated that combinations of analgesic agents can be used in a single dosage form, for example, an opioid analgesic in combination with a non-opioid analgesic. Combinations of hydrocodone or hydromorphone and ibuprofen or acetaminophen are exemplary of such combinations.

Anti-cancer agents, including antineoplastic agents useful in the dosage forms include by way of example paclitaxel, docetaxel, camptothecin and its analogues and derivatives (e.g., 9-aminocamptothecin, 9-nitrocamptothecin, 10-hydroxy-camptothecin, irinotecan, topotecan, 20-O-β-glucopyranosyl camptothecin), taxanes (baccatins, cephalomannine and their derivatives), carboplatin, cisplatin, interferon-$\alpha_{2A}$, interferon-$\alpha_{2B}$, interferon-$\alpha$ $N_3$ and other agents of the interferon family, levamisole, altretamine, cladribine, tretinoin, procarbazine, dacarbazine, gemcitabine, mitotane, asparaginase, porfimer, mesna, amifostine, mitotic inhibitors including podophyllotoxin derivatives such as teniposide and etoposide and *vinca* alkaloids such as vinorelbine, vincristine and vinblastine.

Anti-convulsant (anti-seizure) agents useful in the dosage forms include by way of example azetazolamide, carbamazepine, clonazepam, clorazepate, ethosuximide, ethotoin, felbamate, lamotrigine, mephenytoin, mephobarbital, phenytoin, phenobarbital, primidone, trimethadione, vigabatrin, topiramate, and the benzodiazepines. Benzodiazepines, as is well known, are useful for a number of indications, including anxiety, insomnia, and nausea. Examples of suitable commercially available anti-convulsants useful in the dosage forms of include TEGRETOL® (carbamazepine; Novartis, Summit, N.J.), DILANTIN® (Pfizer Inc., New York, N.Y.) and LAMICTAL® (lamotrigine (GlaxoSmithKline, Philadelphia, Pa.).

Anti-depressant agents useful in the dosage forms include by way of example the tricyclic antidepressants LIMBITROL® (amitriptyline; Hoffmann-LaRoche, Nutley, N.J.), TOFRANIL® (imipramine; Tyco Healthcare, Mansfiled, Mass.), ANAFRANIL™ (clomipramine; Tyco Healthcare, Mansfield, Mass.), and NORPRAMIN® (desipramine; Sanofi-Aventis, Bridgewater, N.J.).

Anti-diabetic agents useful in the dosage forms include by way of example acetohexamide, chlorpropamide, ciglitazone, gliclazide, glipizide, glucagon, glyburide, miglitol, pioglitazone, tolazamide, tolbutamide, triampterine, and troglitazone.

Anti-hyperlipidemic agents useful in the dosage forms include by way of example lipid-lowering agents, or "hyperlipidemic" agents, such as HMG-CoA reductase inhibitors such as atorvastatin, simvastatin, pravastatin, lovastatin and cerivastatin, and other lipid-lowering agents such as clofibrate, fenofibrate, gemfibrozil and tacrine.

Anti-hypertensive agents useful in the dosage forms include by way of example amlodipine, benazepril, darodipine, diltiazem, doxazosin, enalapril, eposartan, esmolol, felodipine, fenoldopam, fosinopril, guanabenz, guanadrel, guanethidine, guanfacine, hydralazine, losartan, metyrosine, minoxidil, nicardipine, nifedipine, nisoldipine, phenoxybenzamine, prazosin, quinapril, reserpine, terazosin, and valsartan.

Anti-inflammatory agents useful in the dosage forms include by way of example nonsteroidal anti-inflammatory agents such as the propionic acid derivatives as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, and fenbufen; apazone; diclofenac; difenpiramide; diflunisal; etodolac; indomethacin; ketorolac; meclofenamate; nabumetone; phenylbutazone; piroxicam; sulindac; and tolmetin, and steroidal anti-inflammatory agents such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone.

Anti-microbial agents useful in the dosage forms include by way of example tetracycline antibiotics and related compounds (chlortetracycline, oxytetracycline, demeclocycline, methacycline, doxycycline, minocycline, rolitetracycline); macrolide antibiotics such as erythromycin, clarithromycin, and azithromycin; streptogramin antibiotics such as quinupristin and dalfopristin; beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriaxone), and carbapenems such as imipenem, meropenem and aztreonam; aminoglycoside antibiotics such as streptomycin, gentamicin, tobramycin, amikacin, and neomycin; glycopeptide antibiotics such as teicoplanin; sulfonamide antibiotics such as sulfacetamide, sulfabenzamide, sulfadiazine, sulfadoxine, sulfamerazine, sulfamethazine, sulfamethizole, and sulfamethoxazole; quinolone antibiotics such as ciprofloxacin, nalidixic acid, and ofloxacin; anti-mycobacterials such as isoniazid, rifampin, rifabutin, ethambutol, pyrazinamide, ethionamide, aminosalicylic, and cycloserine; systemic antifungal agents such as itraconazole, ketoconazole, fluconazole, and amphotericin B; antiviral agents such as acyclovir, famcicyclovir, ganciclovir, idoxuridine, sorivudine, trifluridine, valacyclovir, vidarabine, didanosine, stavudine, zalcitabine, zidovudine, amantadine, interferon alpha, ribavirin and rimantadine; and miscellaneous antimicrobial agents such as chloramphenicol, spectinomycin, polymyxin B (colistin), bacitracin, nitrofurantoin, methenamine mandelate and methenamine hippurate.

Anti-viral agents useful in the dosage forms include by way of example the antiherpes agents acyclovir, famciclovir, foscarnet, ganciclovir, idoxuridine, sorivudine, trifluridine, valacyclovir, and vidarabine; the antiretroviral agents didanosine, stavudine, zalcitabine, and zidovudine; and other antiviral agents such as amantadine, interferon alpha, ribavirin and rimantadine.

Anxiolytics and tranquilizers useful in the dosage forms include by way of example benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, chlordiazepoxide, and droperidol.

Cardiac agents, which can be used in combination with diuretics, useful in the dosage forms include by way of example amiodarone, amlodipine, atenolol, bepridil, bisoprolol bretylium, captopril, carvedilol, diltiazem, disopyramide, dofetilide, enalaprilat, enalapril, encainide, esmolol, flecainide, fosinopril, ibutilide, inamrinone, irbesartan, lidocaine, lisinopril, losartan, metroprolol, nadolol, nicardipine, nifedipine, procainamide, propafenone, propranolol, quinapril, quinidine, ramipril, trandolapril, and verapamil.

Cardiovascular agents useful in the dosage forms include by way of example angiotensin converting enzyme (ACE) inhibitors, cardiac glycosides, calcium channel blockers, beta-blockers, antiarrhythmics, cardioprotective agents, and angiotensin II receptor blocking agents. Examples of the foregoing classes of drugs include the following: ACE inhibitors such as enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl) amino-2,3,4,5-tetrahydro-2-oxo-3S-1H-1-benzazepine-1-acetic acid or 3-(1-ethoxycarbonyl-3-phenyl-(1S)-propylamino)-2,3,4,5-tetrahydro-2-oxo-(3S)-benzazepine-1-acetic acid monohydrochloride; cardiac glycosides such as digoxin and digitoxin; inotropes such as amrinone and milrinone; calcium channel blockers such as verapamil, nifedipine, nicardipene, felodipine, isradipine, nimodipine, bepridil, amlodipine and diltiazem; beta-blockers such as atenolol, metoprolol; pindolol, propafenone, propranolol, esmolol, sotalol, timolol, and acebutolol; antiarrhythmics such as moricizine, ibutilide, procainamide, quinidine, disopyramide, lidocaine, phenytoin, tocainide, mexiletine, flecainide, encainide, bretylium and amiodarone; and cardioprotective agents such as dexrazoxane and leucovorin; vasodilators such as nitroglycerin; and angiotensin II receptor blocking agents such as losartan, hydrochlorothiazide, irbesartan, candesartan, telmisartan, eposartan, and valsartan.

CNS and respiratory stimulants useful in the dosage forms include by way of example xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride.

Hypnotic agents and sedatives useful in the dosage forms include by way of example clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental).

Muscarinic receptor agonists and antagonists useful in the dosage forms include by way of example choline esters such as acetylcholine, methacholine, carbachol, bethanechol (carbamylmethylcholine), bethanechol chloride, cholinomimetic natural alkaloids and synthetic analogs thereof, including pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methyl bromide, ipratropium, methantheline, methscopolamine and tiotropium.

Neuroleptic agents useful in the dosage forms include by way of example antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as nefazodone, trazodone and venlafaxine, and wherein antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole.

Peptide drugs useful in the dosage forms include by way of example the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, vasoactive intestinal peptide (VIP), and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin. Still other peptidyl drugs that can be advantageously delivered using the present systems include endorphins (e.g., dermorphin, dynorphin, α-endorphin, β-endorphin, γ-endorphin, α-endorphin, [Leu$^5$]enkephalin, [Met$^5$]enkephalin, substance P), kinins (e.g., bradykinin, potentiator B, bradykinin potentiator C, kallidin), LHRH analogues (e.g., buserelin, deslorelin, fertirelin, goserelin, histrelin, leuprolide, lutrelin, nafarelin, tryptorelin), and the coagulation factors, such as α$_1$-antitrypsin, α$_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, and thrombomodulin and combinations thereof.

Sex steroids useful in the dosage forms include by way of example progestogens such as acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethyiprogesterone, hydroxymethyiprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Also included within this general class are estrogens, e.g.: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Androgenic agents, also included within the general class of sex steroids, are drugs such as the naturally occurring androgens androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone.

Where appropriate, any of the active agents described herein may be administered in the form of a salt, ester, amide, prodrug, conjugate, active metabolite, isomer, fragment, analog, or the like, provided that the salt, ester, amide, prodrug, conjugate, active metabolite, isomer, fragment, or analog is pharmaceutically acceptable and pharmacologically active in the present context. Salts, esters, amides, prodrugs, conjugates, active metabolites, isomers, fragments, and analogs of the agents may be prepared using standard procedures known to those skilled in the art of synthetic organic chemistry and described, for example, by J. March, *Advanced Organic Chemistry: Reactions, Mechanisms and Structure,* 5th Edition (New York: Wiley-Interscience, 2001). For example, where appropriate, any of the compounds described herein may be in the form of a prodrug. The prodrug requires conversion to the active agent.

Where appropriate, any of the compounds described herein may be in the form of a pharmaceutically acceptable salt. A pharmaceutically acceptable salt may be prepared from any pharmaceutically acceptable organic acid or base, any pharmaceutically acceptable inorganic acid or base, or combinations thereof. The acid or base used to prepare the salt may be naturally occurring.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glutamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Any of the compounds described herein may be the active agent in a formulation as described herein. Formulations may include one, two, three, or more than three of the active agents and drugs described herein, and may also include one or more active agents not specifically recited herein.

When a dosage form or method is used or practiced in combination with the administration of another agent, such as secondary analgesics, anticonvulsant agents, antidepressants, and the like, the additional agent may be obtained from a commercial source in a variety of dosage forms (e.g., tablets, capsules, oral suspensions, and syrups). The additional agent may be administered as a separate dosage form or a gastric retentive dosage form of the present invention may comprising the additional agent may be used.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

EXAMPLES

The following examples illustrate certain aspects and advantages of the present invention, however, the present invention is in no way considered to be limited to the particular embodiments described below.

Example 1

Formulation of LC4SL (L4-4) Tablets

A gastric-retentive dosage form, referred to as LC4SL, was formulated as a single layer tablet to provide sustained release of levodopa and carbidopa into the stomach over a period of approximately four hours. The dosage form having 200 mg levodopa and 54 mg carbidopa had a total weight of 700 mg. The tablet contained 25 wt % POLYOX™1105 (with a molecular weight of approximately 900,000) and approximately 27 wt % microcrystalline cellulose. A high shear granulation of the levodopa and carbidopa were dry blended with the excipients which are listed in Table 1 below. Tablets were then manufactured using a Carver Press with a 0.3937"×0.6299" MOD OVAL die.

TABLE 1

| Ingredients | % of Active Layer | mg/tablet |
|---|---|---|
| Levodopa, USP | 28.57 | 200.0 |
| Carbidopa, USP | 7.71 | 54.0 |
| Povidone, USP [Plasdone K-29/32] | 1.09 | 7.6 |
| Avicel ® Microcrystalline Cellulose NF Ph. Eur. JP | 26.63 | 186.4 |
| Polyethylene Oxide NF [SENTRY ™ POLYOX ™ 1105 LEO NF Grade | 25.00 | 175.0 |
| Mannitol, USP (Pearlitol 200 SD) | 10.00 | 70.0 |
| Magnesium Stearate NF, Non-Bovine | 1.00 | 7.0 |
| Total | 100.00 | 700.0 |

Example 2

Formulation of the LC6SL (L4-6) Tablets

The L4-6 gastric-retentive dosage form was formulated as a single layer tablet to provide sustained release of levodopa and carbidopa into the stomach over a period of approximately six hours. The dosage form having 200 mg levodopa and 54 mg carbidopa had a total weight of 700 mg. The tablet contained approximately 61.6 wt % POLYOX™1105 (with a molecular weight of approximately 900,000). A high shear granulation of the levodopa and carbidopa were dry blended with the excipients, detailed in Table 2 below. Tablets were then manufactured using a Carver Press with a 0.3937"×0.6299" MOD OVAL die.

TABLE 2

| Ingredients | % of Active Layer | mg/tablet |
|---|---|---|
| Levodopa, USP | 28.57 | 200.0 |
| Carbidopa, USP | 7.71 | 54.0 |

TABLE 2-continued

| Ingredients | % of Active Layer | mg/tablet |
|---|---|---|
| Povidone, USP [Plasdone K-29/32] | 1.09 | 7.6 |
| Polyethylene Oxide NF [SENTRY™ POLYOX™ 1105 LEO NF Grade] | 61.63 | 431.4 |
| Magnesium Stearate NF, Non-Bovine | 1.00 | 7.0 |
| Total | 100.00 | 700.0 |

Example 3

Formulation of the LC6BL (L4-6 Bi-Layer) Bilayer Tablets

The L4-6 Bilayer gastric-retentive dosage form was formulated as a bilayer tablet to provide sustained release of levodopa and carbidopa into the stomach over a period of approximately six hours. The full dose of levodopa (200 mg) and carbidopa (54 mg) is present in the first layer which contains about 46.7 wt % Polyox 1105. The tablet contained approximately 61.6 wt % POLYOX™1105 (with a molecular weight of approximately 900,000). A high shear granulation of the levodopa and carbidopa were dry blended with the excipients. The components for the active layer of this bilayer tablet are listed in Table 3 below. The second layer (swelling layer) contained 98.5 wt % POLYOX™ WSR-303 as a swellable gastric retentive layer to further promote retention of the dosage form in the stomach. In the formulation described herein, POLYOX™ WSR-303 TG was used in the second layer, however, POLYOX™ WSR-303 FP may also be used. The bilayer dosage form had a total weight of 700 mg. The ingredients for the swelling layer are listed below in Table 4. Tablets were manufactured using a Carver Press with a 0.3937"×0.6299" MOD OVAL die.

TABLE 3

| Ingredients (Active Layer) | % of Active Layer | mg/tablet |
|---|---|---|
| Levodopa, USP | 40.00 | 200.0 |
| Carbidopa, USP | 10.80 | 54.0 |
| Povidone, USP [Plasdone K-29/32] | 1.52 | 7.6 |
| Polyethylene Oxide NF [SENTRY™ POLYOX™ 1105 LEO NF Grade] | 46.68 | 233.4 |
| Magnesium Stearate NF, Non-Bovine | 1.00 | 5.0 |
| Total | 100.00 | 500.0 |

TABLE 4

| Ingredients (Swelling Layer) | % of Active Layer | mg/tablet |
|---|---|---|
| Polyethylene Oxide NF [SENTRY™ POLYOX™ 1105 LEO NF Grade] | 98.50 | 295.5 |
| Opadry, Blue [YS-1-10699] | 1.00 | 3.0 |
| Magnesium Stearate NF, Non-Bovine | 0.5 | 1.5 |
| Total | 100.00 | 300.0 |

Example 4

In-Vitro Dissolution Release Profiles

Figure 2:
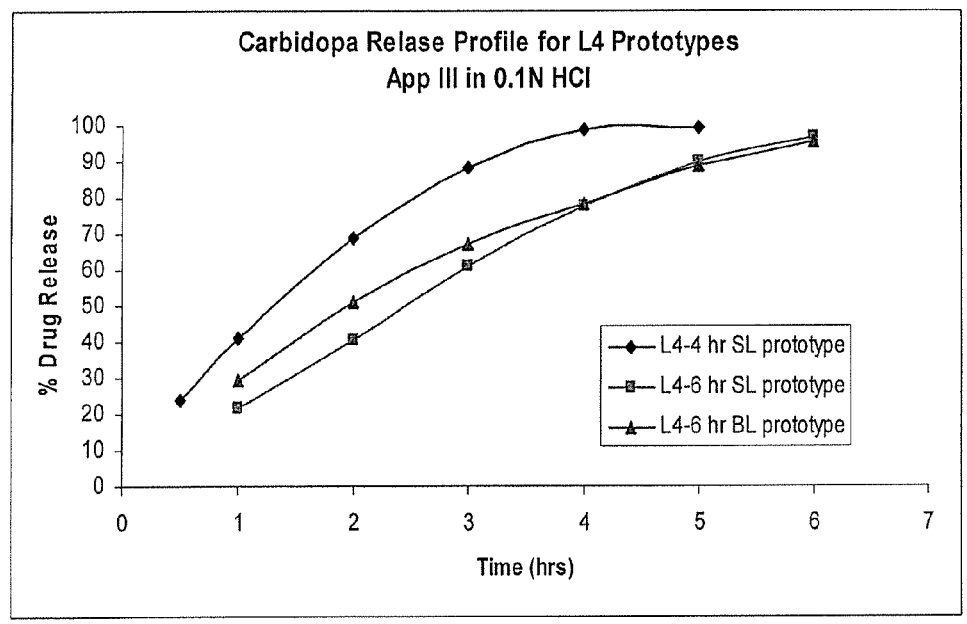
FIG. 2 shows the in vitro release profile for carbidopa release from the LC4SL dosage form as determined using a USP Dissolution Apparatus III at 37.0±0.5° C.

In vitro dissolution release profiles of levodopa and carbidopa release from the LC4SL, LC6SL and LC6BL tablets manufactured as described above were determined using a USP Dissolution Apparatus III (Vankel Bio-Dis, Varian, Cary, N.C.) containing a dissolution medium of 250 ml 0.1N HCl per vessel at 37.0±0.5° C. Samples were taken without media replacement at 1, 2, 3, 4, 5 and 6 hours. The dissolution samples from the stated time-points were analyzed for levodopa and carbidopa, respectively by HPLC using a C18 HPLC column (4.6 mm×15 cm, 5 µm particle size from Thermo Scientific) with column temperature at 25° C., flow rate of 1.0 ml per minute, at a detection wavelength of 280 nm. Results for levodopa release are shown in FIG. 1. Results for carbidopa release are presented in FIG. 2.

Example 5

In-Vitro Dissolution Comparison

Dissolution testing was also performed to compare release profiles from the gastric retentive dosage forms formulated as described herein with the release profiles of levodopa/carbidopa sustained release tablets currently available on the market. Specifically, SINEMET® CR tablets manufactured by Merck & Co. (Whitehouse Station, N.J.), Inc., and levodopa/carbidopa tablets manufactured by Mylan Pharmaceuticals, Inc (Morgantown, W. Va.). Testing was done using a USP Dissolution Apparatus III (Vankel Bio-Dis, Varian, Cary, N.C.) containing a dissolution medium of 250 ml 0.1N HCl per vessel at temperature of 37.0±0.5° C. with reciprocating speed of 30 dips per minute. The dissolution sampling time-points were: 0.08, 0.25, 0.5, 1, 2.5, and 4 hours for Tablets from Mylan and Merck; 0.5, 1, 2, 3, and 4 hours for LC4SL tablets; 1, 2, 3, 4, and 5 hours for the LC6SL tablets; and 1, 2, 3, 5, and 7 hours for the LC6BL tablets. The dissolution samples from the stated time-points were analyzed for levodopa and carbidopa, respectively by HPLC using a C18 HPLC column (4.6 mm×15 cm, 5 µm particle size from Thermo Scientific) with column temperature at 25° C., flow rate of 1.0 ml per minute, at a detection wavelength of 280 nm.

Figure 3:
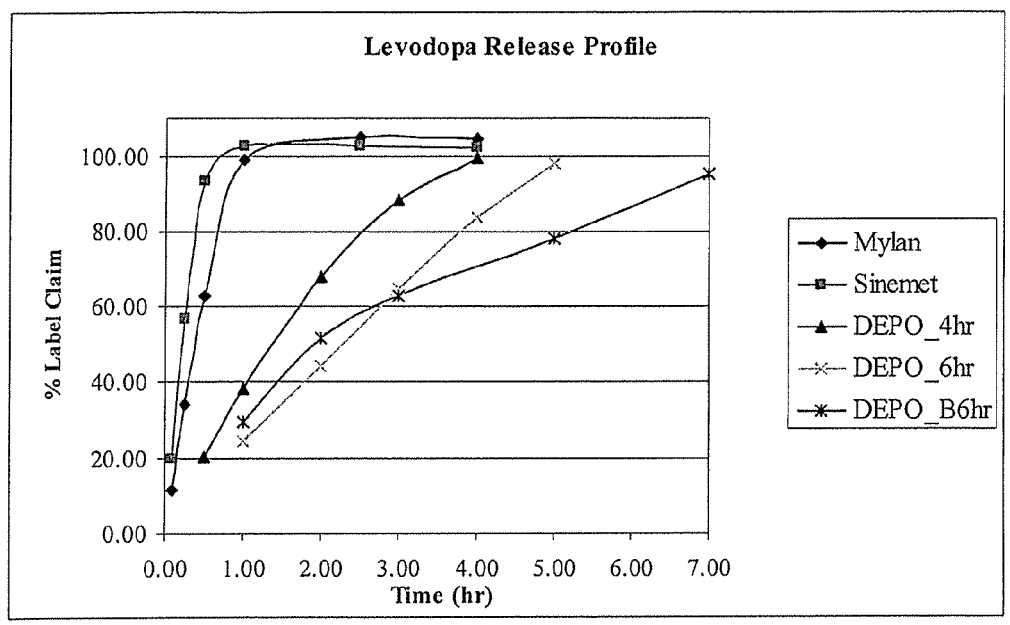
FIG. 3 shows the in vitro release profile for levodopa release from the LC4SL, LC6SL, LC6BL, Mylan and Sinemet CR dosage forms as determined using a USP Dissolution Apparatus III at 37.0±0.5° C.

Results of the dissolution testing are presented below in Table 5 and graphically represented in FIG. 3. Values in Table 5 represent the amount of levodopa released from each dosage form at the specified time period in terms of percent of the label claim (% LC).

TABLE 5

| | % Label Claim for Levodopa | | | | |
|---|---|---|---|---|---|
| Time (h) | Mylan | Sinemet | LC4SL | LC6SL | LC6BL |
| 0.08 | 11.46 | 20.05 | — | — | — |
| 0.25 | 34.28 | 56.96 | — | — | — |
| 0.50 | 63.01 | 93.50 | 20.24 | — | — |
| 1.00 | 98.79 | 102.79 | 38.26 | 24.43 | 29.78 |
| 2.00 | — | — | 67.82 | 44.50 | 51.55 |
| 2.50 | 104.85 | 102.50 | — | — | — |
| 3.00 | — | — | 88.43 | 64.73 | 63.05 |
| 4.00 | 104.52 | 102.05 | 99.53 | 83.84 | — |
| 5.00 | — | — | — | 98.21 | 78.01 |
| 7.00 | — | — | — | — | 95.18 |

Example 6

Erosion and Pharmacokinetic Studies in Dogs

A four-way randomized study was performed in dogs to evaluate the relative bioavailability and pharmacokinetics of levodopa following oral administration of gastric retentive (GR) controlled-release dosage forms of levodopa/carbidopa (LC4SL, LC6SL and LC6BL) as compared to the marketed controlled-release levodopa/carbidopa formulations (Sinemet® CR) manufactured by Merck & Co., Inc. and Mylan Pharmaceuticals, Inc. The study utilized beagle dogs.

This randomized 4-way crossover study was carried out using five healthy female beagle dogs, each weighing 12-16 kg. Following an overnight fast of at least 14 hr the animals were administered 200 mg carbidopa. Forty-five minutes later they were fed 100 gm of canned dog food (Pedigree Traditional Ground Dinner with Chunky Chicken) and administered a single oral dosage of a LC4SL, LC6SL or LC6BL tablet containing 200 mg levodopa and 50 mg carbidopa, or a marketed extended-release formulation containing 200 mg levodopa/50 mg carbidopa (Sinemet® CR). The treatments were administered within 15 minutes of the animals consuming the meal. There was at least one week between administrations to allow for recovery from blood sampling and washout.

The LC4SL, LC6SL and LC6BL tablets were manufactured according to the methods described in Examples 1-3, with the exception that radio-opaque strings were placed in the center of the tablets in the shape of an "X" to act as a marker for gastrointestinal transit and erosion of the tablet. The tablets were tested in vitro to determine their release rate using an USP Dissolution Apparatus III and compared to that of Sinemet CR.

A randomized schedule was employed to administer four different dosage forms containing 200 mg levodopa and 50 mg carbidopa to the dogs. Dosage form A was SINEMET® CR, manufactured by Merck & Co., Inc. Dosage Form B was the LC4SL tablet, Dosage Form C was the LC6SL tablet and Dosage Form D was the LC6BL bilayer tablet.

The randomization schedule is described in Table 6 below. Each period represents one week. Each dog received each of the Dosage Forms A-D, being administered one of the dosage forms at the beginning of a one week period.

TABLE 6

| Dog # | Period 1 | Period 2 | Period 3 | Period 4 |
|---|---|---|---|---|
| 1 | A | D | C | B |
| 2 | D | C | B | A |
| 3 | C | D | A | B |
| 4 | B | A | D | C |
| 5 | A | B | C | D |

Erosion of the GR dosage forms was monitored by fluoroscopy with images obtained every 30 minutes until the tablet completely disintegrated. Physical separation of the strings was considered to representing the time of complete disintegration of the tablets.

Individual and mean tablet erosion times are presented in Table 7. Also presented in Table 7 is the predicted human erosion time for comparison. Predicted human erosion time is based on previous studies of GR formulations where both dog and human erosion studies were conducted on the same formulation. These studies resulted in determination of the mathematical relationship, $HE = DE \times 1.5 + 1.3$, where HE is human erosion time and DE is dog erosion time.

The in vivo erosion studies indicate that the LC4SL formulations will have a levodopa delivery time of approximately 6-7 hours in humans and the LC6SL 6 hour formulation will have a delivery time of about 10 hours.

TABLE 7

| Tablet | Dog 1 | Dog 2 | Dog 3 | Dog 4 | Dog 5 | Mean ± SD | Predicted Human |
|---|---|---|---|---|---|---|---|
| LC4SL | 3.75 | 3.75 | 3.25 | 4.75 | 3.25 | 3.75 ± 0.61 | 6.93 ± 1.06 |
| LC6SL | 6.75 | 5.75 | 6.75 | 3.75 | 7.75 | 6.15 ± 1.52 | 10.53 ± 2.27 |
| LC6BL | 5.25 | 5.25 | 6.25 | 4.75 | 6.25 | 5.55 ± 0.67 | 9.63 ± 1.01 |

To measure levels of levodopa and carbidopa in the plasma after administration of the tablets, 3 ml blood samples were collected in 5 ml Vacutainer® (BD) tubes containing 0.057 ml of 15% (K3) EDTA (anticoagulant) for determination of levodopa concentrations in plasma. Samples were drawn via venipuncture from the cephalic veins at 0.5 h, 1.0 h, 2.0 h, 3.0 h, 4.0 h, 5.0 h, 6.0 h, 7.0 h, 8.0 h, 10.0 h, and 12.0 h after dosing.

Immediately after collection the tube was gently inverted several times to mix the anticoagulant with the blood sample. The samples were then centrifuged at 4-8° C. for 10 minutes at 1,500 rpm. Then 1 ml of the plasma fraction was pipetted into polypropylene cryo-tubes containing 5 mg sodium metabisulfite (stabilizing agent) and mixed thoroughly and then immediately frozen at −80° C. All sample collection and cryo-tubes were labeled to identify the subject, study date, time point, and period.

All plasma samples were stored frozen at −80° C. until shipment. Prior to shipping, the samples were packed into thermal insulated containers with sufficient dry ice to assure they remain frozen during shipment (at least 72 hr). Samples were shipped by overnight, priority courier to BASi (West Lafayette, Ind.).

Levodopa was extracted from dog plasma by an automated solid phase alumina extraction procedure. Before the extraction, N-methyldopamine hydrochloride was added as an internal standard. The extract was injected into an HPLC system with electrochemical detection using an LC-18-DB ODS column with an ion-pairing reagent phosphate buffered mobile phase. The concentration range of the method was 10 ng/ml to 2,000 ng/ml.

Non-compartmental calculations using the linear trapezoidal rule were used to determine the area under the curve from 0 to 12 hours ($AUC_{0-12}$), while the maximum concentration ($C_{max}$) and time to maximum concentration ($t_{max}$) were determined by inspection of the data. Relative bioavailability of the GR formulations to the comparator was calculated by dividing the $AUC_{0-12}$ of the GR tablets by the comparator's $AUC_{0-12}$. In addition, the time the plasma concentration was equal to or greater than 1500 ng/ml was determined for the GR tablets and compared to Sinemet CR. Values below the limit of quantitation for the assay were assumed to be zero for purposes of calculation.

All data presented herein are expressed as either the mean±standard deviation or as the median. One-way ANOVA with repeat measures was used to determine whether there was a difference between mean values. When a difference was found, the Dunnett's test was used to determine which GR formulation means were different from Sinemet CR for PK data. Likewise in the erosion studies the 6 hr formulations were compared to the 4 hr formulation using the Dunnett's test. A p-value of ≤0.05 was considered to indicate a significant difference.

Figure 4:
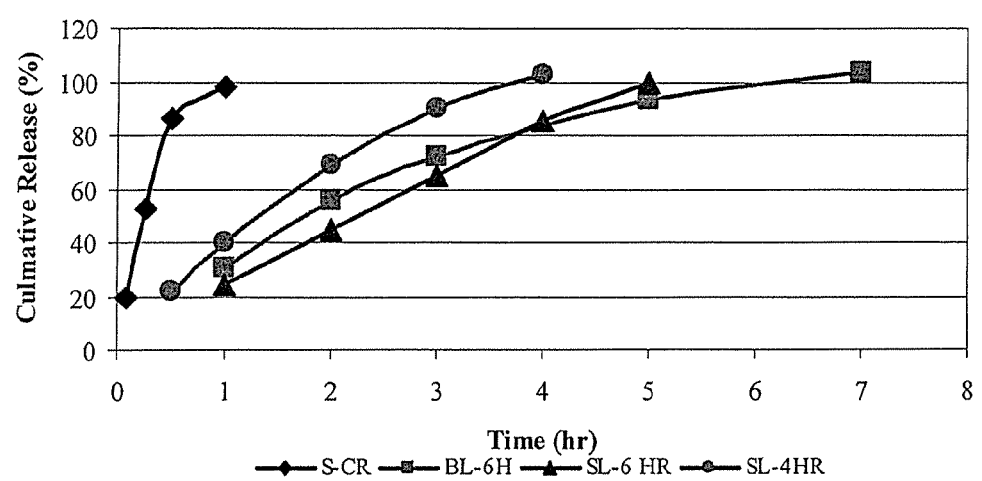
FIG. 4 shows the cumulative release profiles for levodopa release from the LC4SL, LC6SL, LC6BL, and SINEMET® CR dosage forms.

Release profiles as determined by in vitro dissolution testing of the three GR formulations in comparison to Sinemet CR are illustrated in FIG. 4. Under the test conditions Sinemet CR (S-CR) completely released levodopa within one hour. In comparison the SL-4H GR tablets (SL-4HR) had nearly linear release of levodopa though 4 hour and the SL-6H GR tablets (SL-6 HR) had a linear release through 5 hour. The BL-6H GR tablets (BL-6H) had a somewhat faster release of levodopa in the early time points and then the release slowed at later time points resulting in complete release in 6-7 hours.

Figure 5:
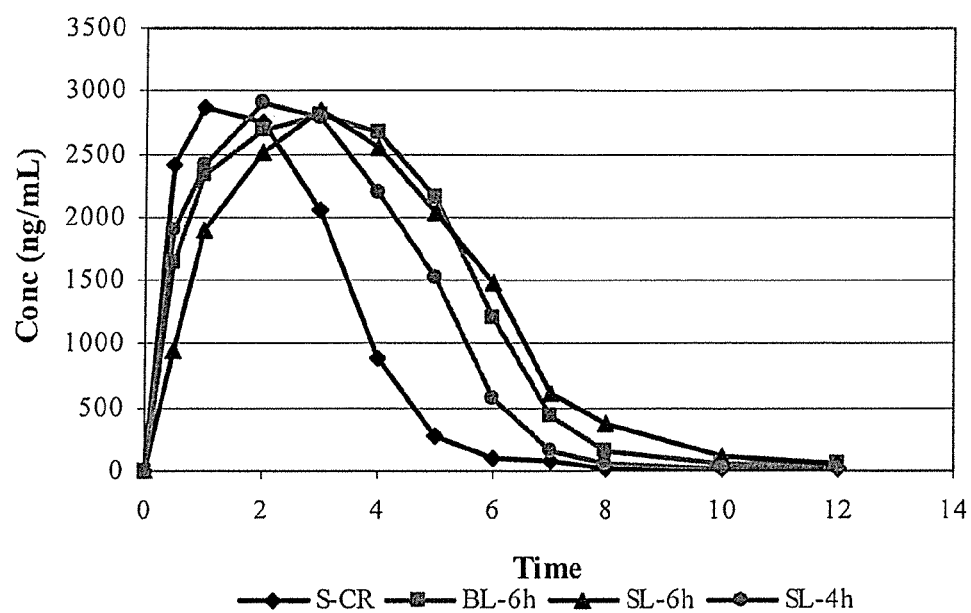
FIG. 5 shows the mean levodopa plasma concentration time profiles for the LC4SL, LC6SL, LC6BL, and SINEMET® CR dosage forms administered to five dogs.
Figure 6A:
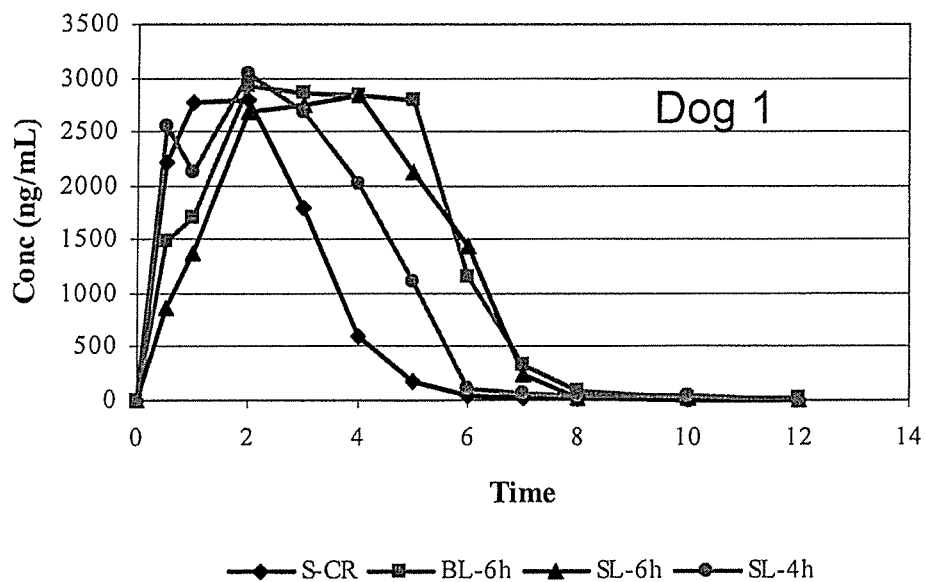
FIG. 6A-E show the individual levodopa plasma concentration time profiles for the LC4SL, LC6SL, LC6BL, and SINEMET® CR dosage forms administered to each of the five dogs.
Figure 6B:
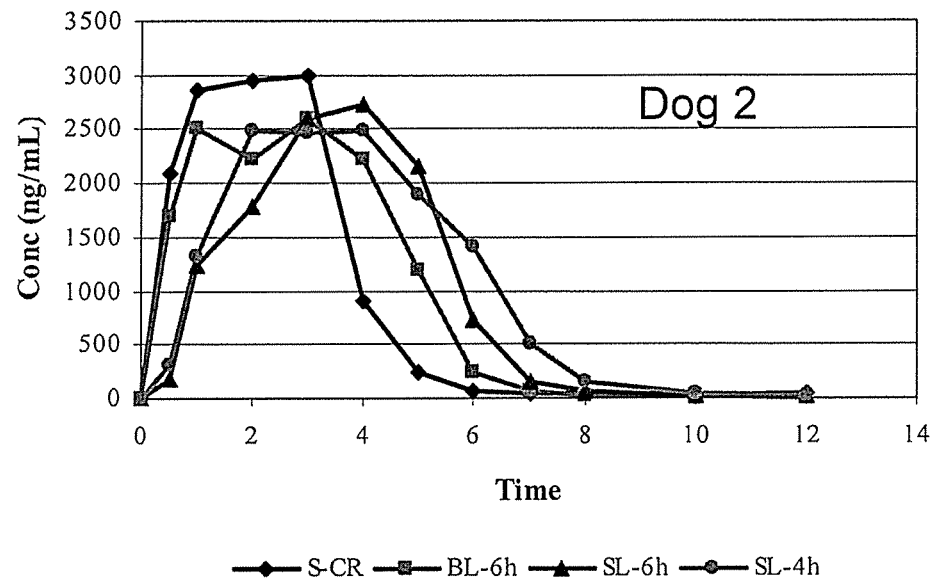
Figure 6C:
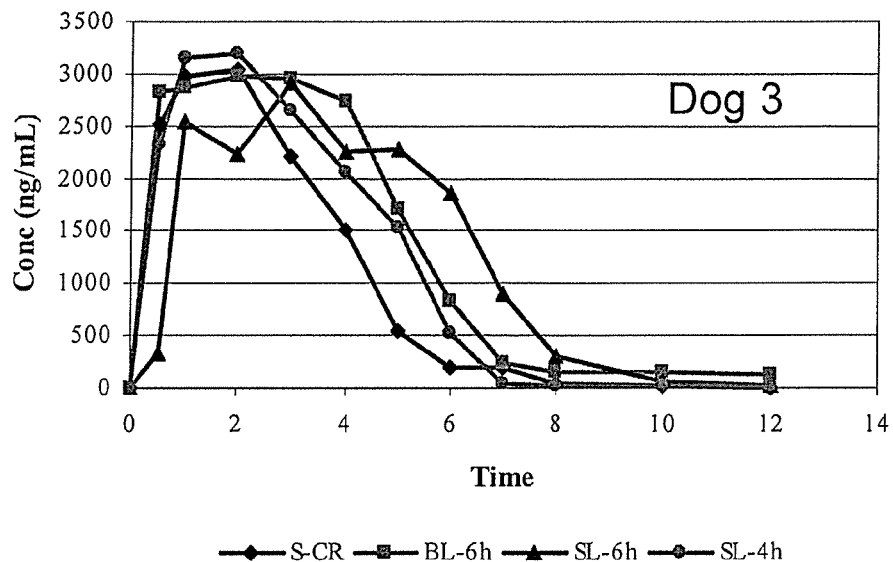
Figure 6D:
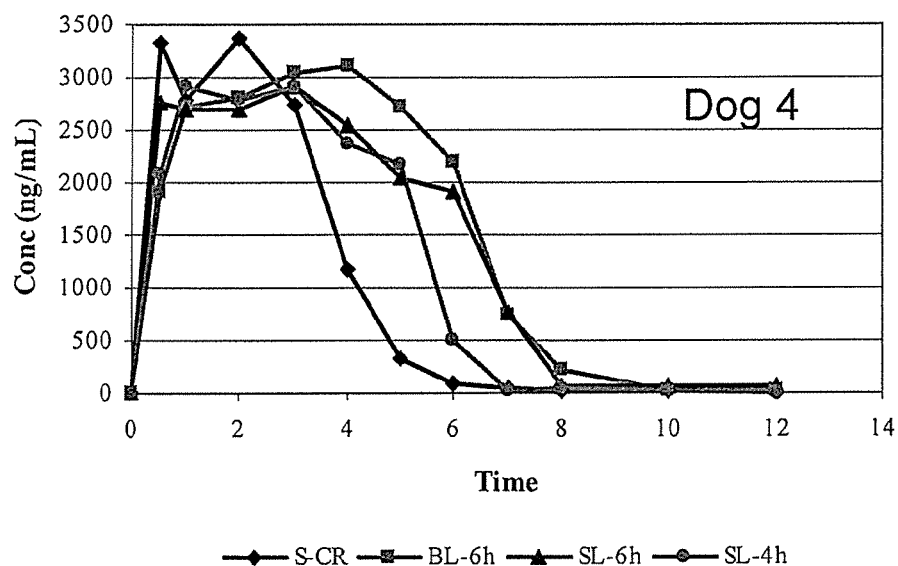
Figure 6E:
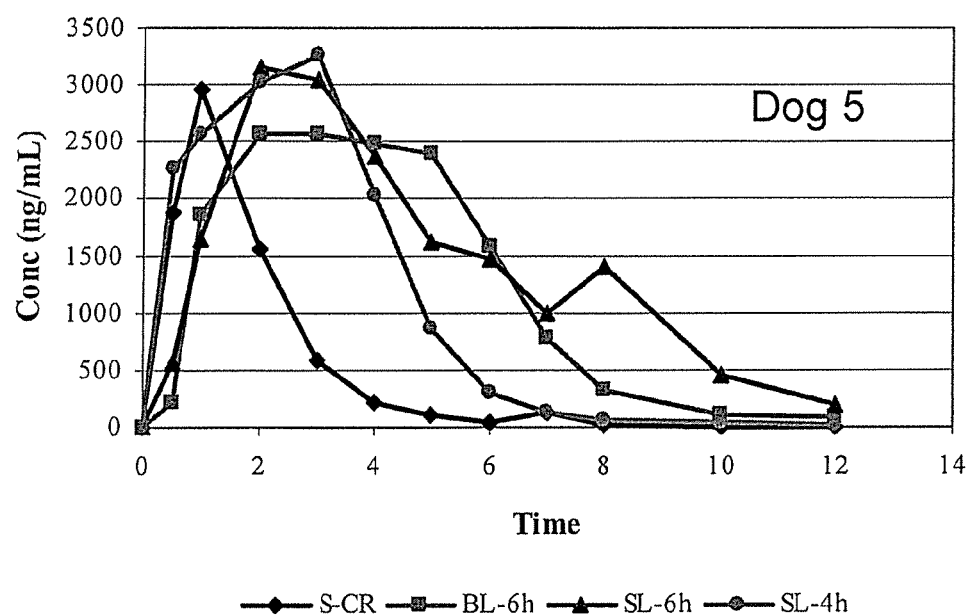

Individual and mean pharmacokinetic parameters for each formulation are listed in Tables 8-11 below, as well as the relative bioavailability for the GR tablets (Table 12). The mean levodopa plasma concentration time profile is illustrated in FIG. 5 and the individual profiles are presented in FIGS. 6A-E. The concentration time profiles of the three dosage forms were typical of an extended-release formulation (FIGS. 3-7). In comparison to Sinemet CR, the AUC of all extended-release GR tablets were significantly higher (Table 8, * indicates where p<0.05 compared to Sinemet CR). $C_{max}$ and $t_{max}$ values were not different from S-CR for the extended-release OR tablets (Tables 9 and 10, respectively 1, p>0.05). However, there was a statistically significant increase in the duration of time the plasma concentration of levodopa was great than 15 ng/ml (Table 11). CV is the coefficient of variation.

TABLE 8

$AUC_{0-12}$ (ng · h/ml)

| Tablet | Dog 1 | Dog 2 | Dog 3 | Dog 4 | Dog 5 | Mean ± SD | CV (%) |
|---|---|---|---|---|---|---|---|
| S-CR | 8662 | 10554 | 11295 | 11531 | 5825 | 9573 ± 2379 | 24.9 |
| LC6BL | 15120 | 11350 | 15655 | 17971 | 14697 | 14959 ± 2381* | 15.9 |
| LC6SL | 13613 | 11297 | 15125 | 16556 | 17379 | 14794 ± 2425* | 16.4 |
| LC4SL | 12015 | 12696 | 13632 | 14045 | 12896 | 13057 ± 798* | 6.1 |

TABLE 9

$C_{max}$ (ng/ml)

| Tablet | Dog 1 | Dog 2 | Dog 3 | Dog 4 | Dog 5 | Mean ± SD | CV (%) |
|---|---|---|---|---|---|---|---|
| S-CR | 2801 | 3000 | 3043 | 3367 | 2969 | 3036 ± 206 | 6.8 |
| LC6BL | 2915 | 2603 | 2970 | 3101 | 2582 | 2834 ± 231 | 8.2 |
| LC6SL | 2840 | 2729 | 2912 | 2914 | 3271 | 2984 ± 308 | 5.5 |
| LC4SL | 3037 | 2494 | 3204 | 2912 | 3271 | 2984 ± 308 | 10.3 |

TABLE 10

$t_{max}$

| Tablet | Dog 1 | Dog 2 | Dog 3 | Dog 4 | Dog 5 | Mean ± SD |
|---|---|---|---|---|---|---|
| S-CR | 2 | 3 | 2 | 2 | 1 | 2.0 ± 0.7 |
| LC6BL | 2 | 3 | 2 | 4 | 2 | 2.6 ± 0.9 |
| LC6SL | 4 | 4 | 3 | 3 | 2 | 3.2 ± 0.8 |
| LC4SL | 2 | 4 | 2 | 3 | 3 | 2.8 ± 0.8 |

TABLE 11

Duration the plasma concentration of levodopa greater than 15 ng/ml (h)

| Tablet | Dog 1 | Dog 2 | Dog 3 | Dog 4 | Dog 5 | Mean ± SD | CV (%) |
|---|---|---|---|---|---|---|---|
| S-CR | 2.88 | 3.26 | 3.69 | 3.46 | 1.70 | 3.00 ± 0.78 | 26.0 |
| LC6BL | 5.26 | 4.17 | 4.89 | 5.04 | 5.15 | 4.90 ± 0.43* | 8.8 |
| LC6SL | 4.79 | 3.97 | 5.54 | 6.02 | 4.98 | 5.06 ± 0.78* | 15.4 |
| LC4SL | 4.21 | 4.69 | 4.69 | 6.16 | 4.12 | 4.77 ± 0.82* | 17.2 |

TABLE 12

% Relative Bioavailability (BA)

| Tablet | Dog 1 | Dog 2 | Dog 3 | Dog 4 | Dog 5 | Mean ± SD | CV (%) |
|---|---|---|---|---|---|---|---|
| LC6BL | 175 | 108 | 139 | 156 | 252 | 166 ± 54 | 32.5 |
| LC6SL | 157 | 107 | 134 | 144 | 298 | 168 ± 75 | 44.6 |
| LC4SL | 139 | 120 | 121 | 122 | 221 | 145 ± 44 | 30.3 |

The concentration time profiles for the levodopa extended-release GR tablets demonstrate a sustained-release profile compared to the extended-release comparator (Sinemet CR). In addition, the relative bioavailability compared to Sinemet CR was significantly increased, while the $C_{max}$ and $t_{max}$ values were not different. Although the $t_{max}$ values were not as different as might be expected with a longer release profile, the time the levodopa concentration was greater than 1500 ng/ml was significantly increased. This indicates the plateau was maintained for a significantly longer period and may result in more constant levodopa blood levels at steady state.

The PK profiles of the levodopa extended-release GR tablets also tended to follow the in vitro release profiles. The LC4SL (SL-4H) tablet demonstrated a rapid rise to $C_{max}$ which is consistent with the quicker in vitro release. The LC6BL (BL-6H) tablet also demonstrated a more rapid rise to $C_{max}$ than the LC6SL (SL-6H), which is also consistent with their in vitro release profiles. In vitro the LC6BL tablet demonstrated a more rapid release at early time point and then slowed its release while the LC6SL tablet demonstrated a near linear release over time and thus lower levodopa blood concentration at early time point in the concentration time profiles.

The in vivo erosion studies indicate that the LC4SL 4-hour formulation will have a levodopa delivery time of approximately 6-7 hours in humans and the LC6SL 6-hour formulation will have a delivery time of about 10 hours. PK modeling data has indicated that a predicted release time of 7-10 hours may result in twice a day dosing in humans with a relatively constant levodopa blood concentration.

In conclusion, all GR extended formulations extended the release and increased the bioavailability of levodopa compared to SINEMET® CR in Beagle dogs.

Example 7

Phase I Pharmacokinetics Study

An open label, three-way crossover study was done to analyze levodopa/carbidopa tolerability and pharmacokinetics following administration of two Gastric Retentive (GR®) extended release tablets formulated as described herein as compared to administration of a reference extended release tablet currently marketed for treatment of patients with Parkinson's Disease.

The objective of this study was to compare the pharmacokinetic profiles of levodopa and carbidopa delivered from two gastric retentive test formulations of levodopa/carbidopa ER tablets, LC4SL and LC6BL, with from a comparator carbidopa/levodopa extended-release tablet. Parkinson's Disease patients were administered the dosage forms under fed conditions.

This was a randomized, open-label, single-dose, six-sequence, three-treatment, three-period crossover designed in Parkinson's Disease patients. Eighteen men (7) and women (11) at least 30 years of age with a diagnosis of idiopathic Parkinson's disease with stable disease and a modified Hoehn & Yahr stage equal to or less than 3 (Stage 1 unilateral disease, stage 2 mild bilateral disease and stage 3 more advanced bilateral disease) were enrolled. Fifteen minutes after the start of a standardized, approximately 750 calorie (~40% of calories from fat) meal the subjects were administered one of the following test formulations:

Formulation 1: A single layer gastric retentive Levodopa 200 mg/Carbidopa 50 mg Extended Release Tablet with a in vitro release time of 4 hr (LC4SL); Formulation 2: A bilayer layer gastric retentive Levodopa 200 mg/Carbidopa 50 mg Extended Release Tablet with a in vitro release time of 6 hr (LC6BL); Comparator: A commercially available Carbidopa and Levodopa Extended-release Tablet, containing 200 mg levodopa and 50 mg carbidopa (Mylan).

Blood samples were taken prior to administration and at 0.5, 1.0, 1.5, 2.0, 2.5, 3.0, 4.0, 5.0, 6.0, 8.0, 10.0, 12.0, 16.0, and 24.0 hours after oral drug administration. The plasma concentrations of levodopa and carbidopa were analyzed using a validated assay method. There were at least 7 but no more than 14 days between treatment administrations.

Pharmacokinetic analysis employing non-compartmental methods was used to determine the following parameters for levodopa and carbidopa: area under the curve from dose administration to last time point ($AUC_{0-t}$), AUC for dose administration to infinity ($AUC_{0-\infty}$), maximum concentration ($C_{max}$), time to maximum concentration ($t_{max}$), and the terminal half-life ($t_{1/2}$).

Figure 7A:
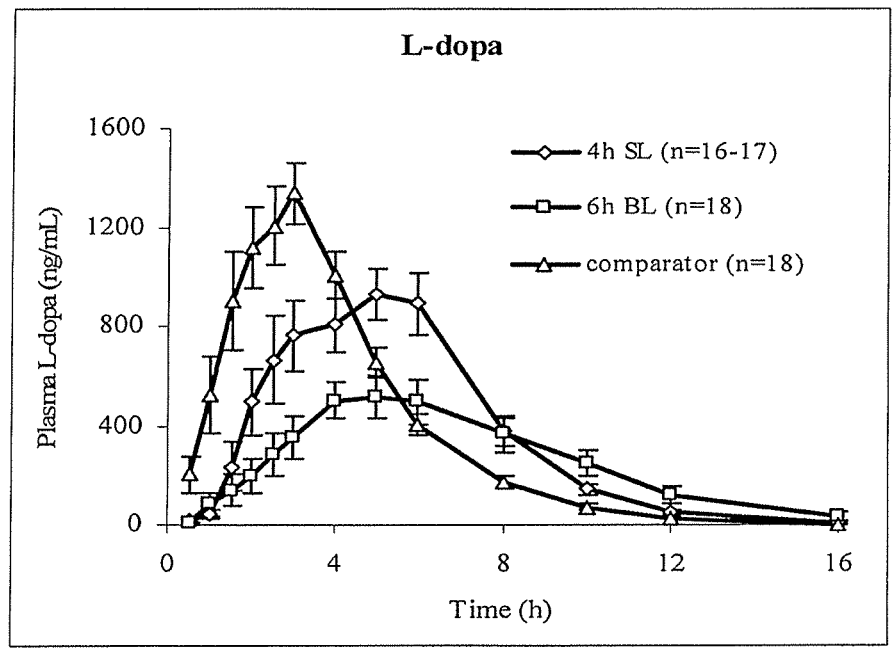
FIG. 7A-B show the plasma concentration time profiles for levodopa (FIG. 7A) and carbidopa (FIG. 7B) for the LC4SL, LC6BL and Mylan dosage forms as determined for human subjects.
Figure 7B:
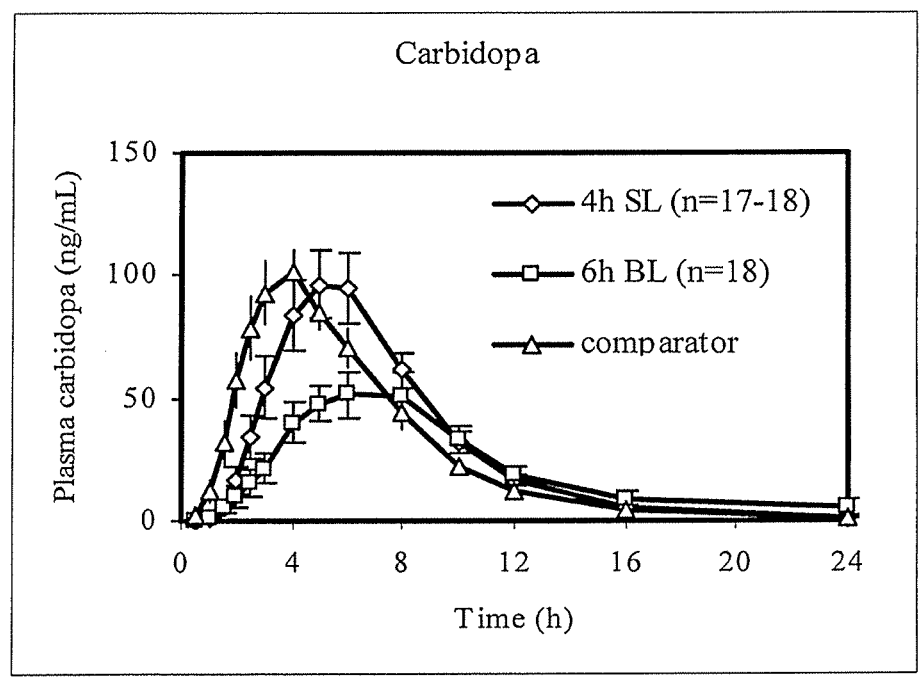

Mean levodopa and carbidopa pharmacokinetic parameters for each formulation are listed in Tables 13 and 14, respectively. The mean levodopa and carbidopa plasma concentration time profiles are illustrated in FIGS. 7A and 7B, respectively. The gastric retentive formulations exhibited an typical extended-release profile with a reduced $C_{max}$ and an extended $t_{max}$ for levodopa compared to the faster releasing comparator formulation. Specifically, results show that the LC4SL extended the median time point at which levodopa blood levels exceeded the efficacious threshold of 300 ng/ml to approximately nine hours, compared to approximately seven hours for the generic (Mylan) version of SINEMET4 CR. The tiem to medidan peak levodopa blood levels in the study was extended to about 4 hours, compared to 2.8 hours for the comparator. Moreover, the bioavailability of levodopa for the single layer 4 hour release formulation relative to the comparator formulation calculated as the ratio of $AUC_{inf}$ for individual subjects is 96±12%. This value is 75±24% for the bilayer 6 hour release formulation.

TABLE 13

| Formulation | Comparator | Formulation 1 (LC4SL) | Formulation 2 (LC6BL) |
|---|---|---|---|
| $t_{max}$ (h) mean (SD) | 3 (1.5-4) | 4 (2-6) | 4.0 (1.5-1.0) |
| $C_{max}$ (ng/ml) | 1659 ± 544 | 1306 ± 496 | 858 ± 392 |
|  | CV = 32.7% | CV = 37.9% | CV = 45.7% |
| $AUC_{0-t}$ (ng · h/ml) | 5806 ± 1967 | 5107 ± 1318 | 4265 ± 1876 |
|  | CV = 33.8% | CV = 25.8% | CV = 44.0% |
| $AUC_{0-\infty}$ (ng · h/ml) | 5852 ± 1968 | 5150 ± 1319 | 4427 ± 1941 |
|  | CV = 33.6% | CV = 25.6% | CV = 43.8% |
| $t_{1/2}$ (h) | 1.7 ± 0.6 | 1.5 ± 0.2 | 2.3 ± 2.0 |

TABLE 14

| Formulation | Comparator | Formulation 1 (LC4SL) | Formulation 2 (LC6BL) |
|---|---|---|---|
| $t_{max}$ (h) mean (SD) | 4 (2-8) | 5 (3-8) | 5 (2-16) |
| $C_{max}$ (ng/ml) | 114 ± 43 CV = 32.7% | 115 ± 66 CV = 57.3% | 71 ± 44 CV = 57.1% |
| $AUC_{0-t}$ (ng · h/ml) | 668 ± 247 CV = 37.0% | 615 ± 238 CV = 38.7% | 475 ± 266 CV = 56.0% |
| $AUC_{0-\infty}$ (ng · h/ml) | 677 ± 247 CV = 36.5% | 622 ± 240 CV = 38.6% | 482 ± 267 CV = 55.4% |
| $t_{1/2}$ (h) | 3.8 ± 1.1 | 3.4 ± 0.7 | 3.4 ± 0.7 |

Example 8

In Vitro-In Vivo Drug Release Correlation

As erosion of tablet matrix is the mechanism for drug release from the three formulations described herein (LC4SL, LC6SL and LC6BL), and the hydrodynamic condition (degree of agitation) of the surrounding fluid environment of the tablet influences this erosion, drug release in vitro determined by dissolution testing was evaluated under various dissolution medium agitation conditions using three different USP apparatuses at various rotation speeds or oscillation rates: USP Apparatus 1 (basket), 100 and 150 revolutions per minute (rpm); USP Apparatus 2 (paddle), 100 and 150 rpm; and USP Apparatus 3 (reciprocating cylinder) at 10, 20, and 30 cycles per minute (cpm). In all cases, the dissolution medium is 0.1 N Hydrochloric acid (HCl), maintained at a temperature of 37±0.5° C. Cumulative drug release over time, represented as percent of labeled claim (% LC) for drug content, is plotted as a function of dissolution medium sampling time.

In vivo drug release is represented by in vivo absorption as levodopa absorption is relatively fast compared with drug release which extends over a period of hours in these formulations. The in viva absorption time profile of levodopa for the three formulations were determined from the plasma concentration time profiles obtained from the clinical pharmacokinetic study using the Wagner-Nelson method (Malcom Rowland, Thomas N. Tozer (Eds.) "Estimation of Adsorption Kinetics from Plasma Concentration Data" in Clinical Pharmacokinetics, pp 480-483, Williams & Wilkins, 1995). Since the measure of cumulative absorption over time derived from this method is the percent of the total amount of drug eventually absorbed, this was multiplied by the bioavailability of the test formulations relative to the comparator formulation (ratio of $AUC_{Inf}$) as an indication of the actual amount of drug absorbed.

Figure 8A:
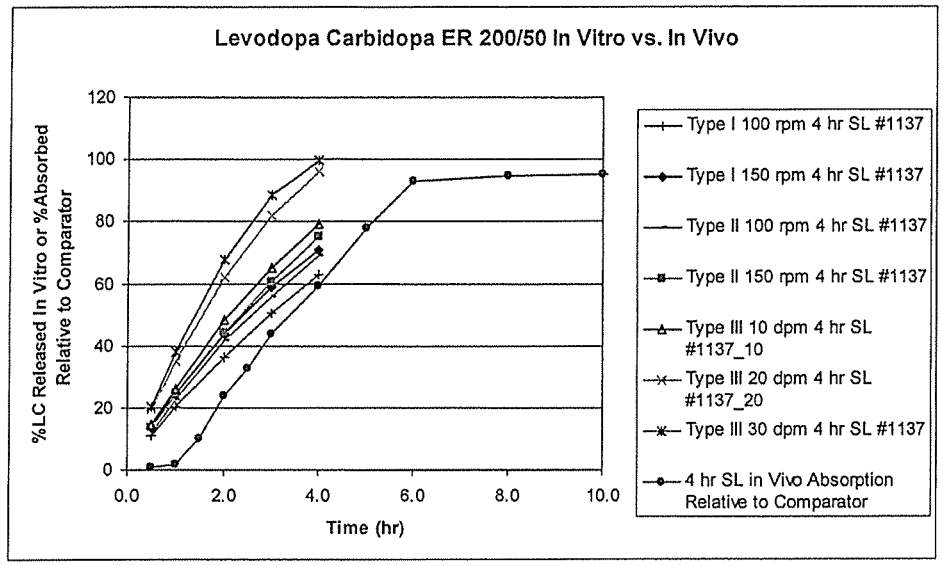
FIG. 8A-E show in vitro release profiles plotted with in vivo absorption profiles as a function of time.
Figure 8B:
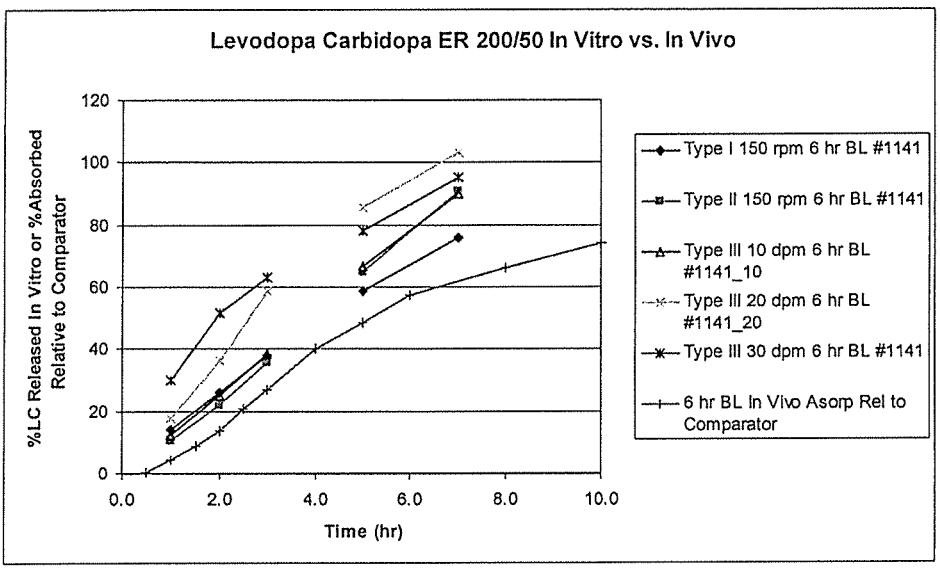
Figure 8C:
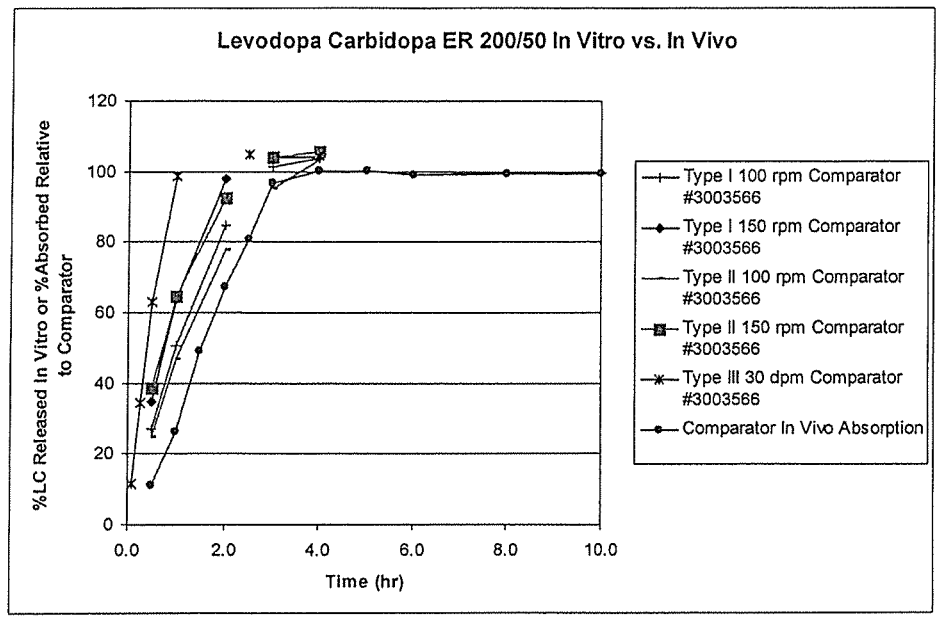
Figure 8D:
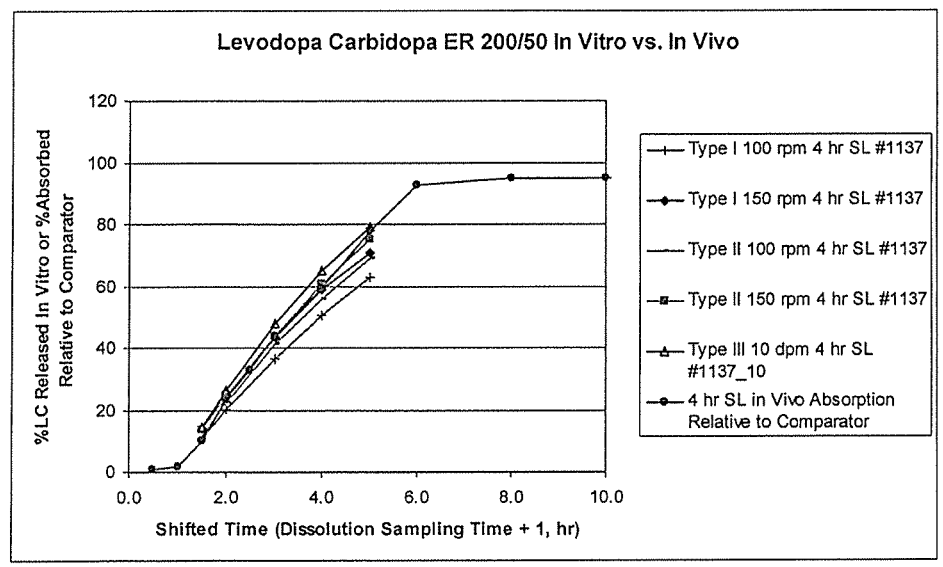
Figure 8E:
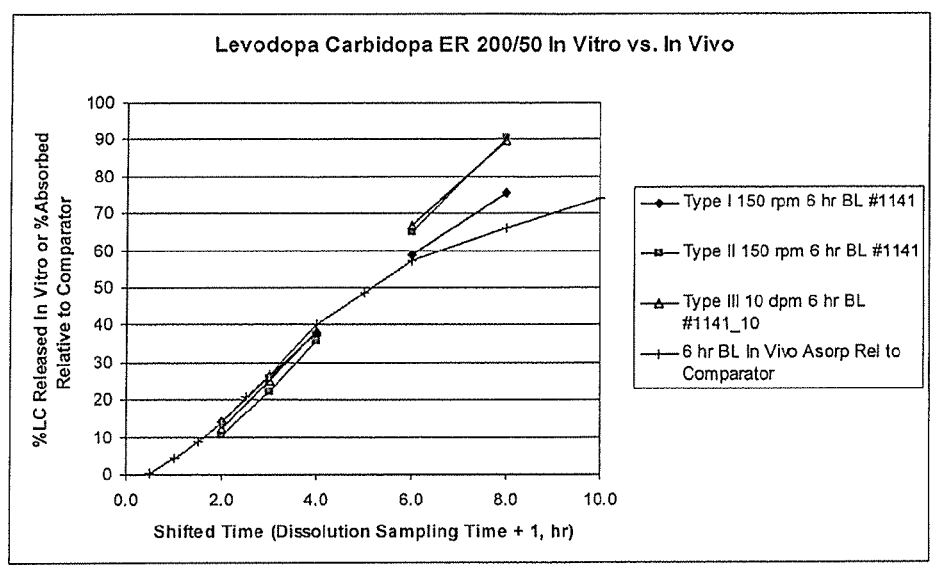

The in vitro drug release profiles and the in vivo absorption profiles are plotted together as a function of time for each formulation (FIGS. 8A, B, and C, respectively). As can be seen from the above figures, in vitro release is higher than in viva at a given time and is higher for higher degrees of medium agitation. However, for Formulation 01 and 03 (LC4SL and LC6BL, respectively) in vitro release profiles obtained from USP Apparatus 1 and 2 at 150 rpm, and USP Apparatus 3 at 10 cpm) have very similar slopes compared to the in vivo absorption profiles. This is more apparent if the in vitro profiles are shifted to the right by 1 hour (FIGS. 8D and 8E), which then almost coincide with the in vivo absorption profiles. As for the comparator formulation, this is case for USP Apparatus 1 and 2 at 100 and 200 rpm and is more apparent with a time shift of 1 hr for 150 rpm profiles and a time shift of 0.5 hr for 100 rpm profiles. These time shifts between in vitro and in vivo profiles seems to be the presence of a time lag in the in vivo absorption profiles.

Example 9

Pharmacokinetic Simulation of Extended Release Levodopa

Pharmacokinetic simulation analysis was performed to predict pharmacokinetic values based on data from the Phase I trial described in Example 7. The data from the Phase I trial were used to calculate the peak and 12-hour post-administration levodopa plasma concentration, as well as the ratio of the mean $C_{max}$ to the mean $C_{12}$ (plasma concentration of levodopa 12 hours after administration) and the mean ratio of $C_{max}$ to $C_{12}$. It can be see from Table 15 that the ratio of $C_{max}$ to $C_{12}$ for the LC4SL formulation is ~50% of that of the comparator. This indicates the likelihood that the fluctuation in plasma concentration at steady state under the same twice daily dosing regimen will be less than that of the comparator by the same magnitude.

TABLE 15

| | Mean peak Plasma Conc. (Cmax, ng/ml) | Mean Plasma Conc. At 12 h (C12 h, ng/ml) | Ratio of Mean Cmax to Mean $C_{12}$ | Mean Ratio* Cmax/C12 h ± SD (CV %) |
|---|---|---|---|---|
| LC4SL | 1306 | 53 | 25 | 27 ± 16 (60) |
| LC6BL | 858 | 121 | 7 | 15 ± 15 (99) |
| Comparator | 1659 | 29 | 57 | 66 ± 21 (32) |

*Individual subjects

The average plasma concentration profiles were fitted to a one-compartment pharmacokinetic model with zero order input and first order elimination for the Comparator and the LC4SL formulation. Zero order release time, apparent volume of distribution, and elimination constants were obtained as fitted parameters and are presented in Table 3.

TABLE 3

| Parameter | Comparator | LC4SL Formulation |
|---|---|---|
| Zero Order Release Time (h) | 3.3 | 6.2 |
| Apparent Volume of Distribution (ml) | 79500 | 77300 |
| Elimination Rate Constant ($h^{-1}$) | 0.429 | 0.469 |
| Elimantion Half-life (h) | 1.62 | 1.48 |

Using these parameters and the method of superposition (Gibaldi & Perrier, 1982, *Pharmacokinetics*, New York: Dekker), average, peak, and trough plasma concentrations at steady state under twice daily or three times daily administrations were predicted for these formulations, and are presented in Table 4.

TABLE 4

|  | Comparator | | | LC4SL | | | Theoretical | |
|---|---|---|---|---|---|---|---|---|
| Total Daily Dose | 200 × 2 | 200 × 3 | 400 × 3 | 200 × 2 | 200 × 3 | 600 × 2 | 600 × 2 | 600 × 2 |
| Individual Dose (mg) | 200 | 200 | 400 | 200 | 200 | 600 | 600 | 600 |
| Zero Order Release Time (h) | 3.3 | 3.3 | 3.3 | 6.2 | 6.2 | 6.2 | 8 | 9 |
| Zero Order Release Rate (mg/h) | 60.6 | 60.6 | 121 | 32.3 | 32.3 | 96.8 | 75.0 | 73.3 |
| Dosing Interval (h) | 12 | 8 | 8 | 12 | 8 | 12 | 12 | 12 |
| Peak Plasma Conc. At Steady state $C_{ss,max}$ (ng/ml) | 1354 | 1391 | 2781 | 844 | 861 | 2533 | 2027 | 1818 |
| Trough Plasma Conc. At Steady state $C_{ss,min}$ (ng/ml) | 32 | 185 | 370 | 56 | 370 | 167 | 311 | 445 |
| Ratio $C_{ss,max}/C_{ss,min}$ | 41.8 | 7.5 | 7.5 | 15.2 | 2.3 | 15.2 | 6.5 | 4.1 |
| Steady state Average Plasma Conc. $C_{ss,avg}$ (ng/ml) | 489 | 733 | 1466 | 460 | 690 | 1379 | 1379 | 1379 |
| Fluctuation (%)* | 270 | 164 | 164 | 172 | 71 | 172 | 124 | 100 |
| Swing (%)** | 4078 | 651 | 651 | 1418 | 133 | 1418 | 553 | 308 |

*Fluctuation (%) = $(C_{ss,max} - C_{ss,min})/C_{ss,avg} \times 100$

**Swing (%) = $(C_{ss,max} - C_{ss,min})/C_{ss,min} \times 100$

Under the same dosing regimen, the simulations show that twice daily (every 12 hours) or three times daily administration (every 8 hours), the LC4SL dosage form has much less fluctuation in plasma concentration over a dosing interval compared to the comparator (172% vs. 270% and 71% vs. 164%), lower $C_{max}$ and higher $C_{min}$, hence a lower ratio, and less swing also. However, when the LC6BL formulation administered twice daily is compared to the Comparator administered three times daily, the trough plasma concentration will be lower despite similar peak and average concentrations and fluctuation (Table 4). Two theoretical formulation cases were also simulated where the zero order release time is extended to 8 and 9 hours for the LC4SL formulation when administered twice daily, with all other parameters being the same. Under these conditions, the LC4SL formulation will have lower peak to trough ratios and fluctuations compared to the Comparator dosed twice daily. The trough concentration for the 8 hr theoretical formulation is somewhat lower (16%) than that of the comparator (311 vs. 370 ng/ml), while that of the 9 hr theoretical formulation is higher (445 ng/ml).

The invention claimed is:

1. A method for treating a subject suffering from a movement disorder, comprising orally administering to said subject an extended release dosage form comprising a polymer matrix,
   wherein the polymer matrix comprises at least one hydrophilic polymer wherein the at least one hydrophilic polymer is present in the polymer matrix in an amount ranging from 20 wt % to 60 wt % and the at least one hydrophilic polymer comprises polyethylene oxide) having a molecular weight of about 900,000 Daltons to 2,000,000 Daltons,
   wherein a first dose of levodopa and a first dose of carbidopa are dispersed in the polymer matrix, and
   wherein the polymer matrix swells upon imbibition of fluid to a size sufficient for gastric retention in the gastrointestinal tract of the subject in a fed mode,
   wherein not more than 40% of the first dose of levodopa and not more than 40% of the first dose of carbidopa are released from the dosage form within about the first hour after administration, and
   wherein at least 80% of the first dose of levodopa and at least 80% of the first dose of carbidopa are released from the dosage form during a period of about 8 hours after oral administration.

2. The method of claim 1, wherein said administering comprises administering the dosage form twice in a 24-hour period, and wherein said administering is with a meal.

3. The method of claim 1, wherein the movement disorder is selected from the group consisting of Parkinson's Disease, Huntington's chorea, residual amblyopia, Angelman Syndrome, progressive supranuclear palsy, Wilson's disease, Tourette's syndrome, epilepsy, and dyskinesia.

4. The method of claim 1, wherein the ratio of the first dose of levodopa to the first dose of carbidopa in the dosage form is between 10:1 and 1:1.

5. The method of claim 1, wherein the dosage form further comprises an antioxidant.

6. The method of claim 1, wherein the polymer matrix of the dosage form is comprised of a mixture of at least two hydrophilic polymers.

7. The method of claim 1, wherein upon administration of the dosage form to the subject, the dosage form imbibes fluid and swells to a size between about 110% to 170% of the dosage form's size prior to administration within 1 hour after the administering.

8. The method of claim 1, wherein between about 10% to about 40% of the levodopa is released from the dosage form within about 1 hour in an in vitro dissolution test.

9. The method of claim 1, wherein the administering produces a plasma profile in the subject comprising:
a prolonged plasma level of levodopa for at least 6-10 hours or 8-12 hours maintaining therapeutic efficacy; and
the $C_{max}$ for levodopa is between about 300 ng/ml to about 1500 ng/ml and a $C_{min}$ for levodopa of between about 300 ng/ml to about 1500 ng/ml.

10. The method of claim 9, wherein when administered to the subject the dosage form provides a ratio of $C_{max}$ to $C_{min}$ for levodopa less than or equal to about four.

11. The method of claim 1, wherein the dosage form further comprises an immediate release portion comprising a second dose of levodopa and a second dose of the carbidopa, both of the second doses dispersed in the immediate release portion, said immediate release portion in contact with said polymer matrix.

12. The method of claim 11, wherein the ratio of the second dose of levodopa to the second dose of carbidopa is between 10:1 and 1:1.

13. The method of claim 11, wherein the dosage form is a bilayer tablet, wherein the immediate release portion is an immediate release layer and the polymer matrix is an extended release layer.

14. The method of claim 11, wherein the administering produces a plasma profile in the subject comprising:
a fast onset plasma level achieved within less than about two hours;
followed by a prolonged plasma level of carbidopa for at least 6-10 hours or 8-12 hours maintaining therapeutic efficacy; and
a $C_{max}$ for levodopa of between about 300 ng/ml to about 1500 ng/ml of levodopa.

15. The method of claim 11, wherein the ratio of the $C_{max}$ to the $C_{min}$ for levodopa is less than or equal to about five.

* * * * *